(12) United States Patent
Voudouris

(10) Patent No.: US 9,320,730 B2
(45) Date of Patent: Apr. 26, 2016

(54) BENDAMUSTINE SOLID DISPERSIONS AND CONTINUOUS INFUSION

(71) Applicant: Vasilios Voudouris, Sacramento, CA (US)

(72) Inventor: Vasilios Voudouris, Sacramento, CA (US)

( * ) Notice: Subject to any disclaimer, the term of this patent is extended or adjusted under 35 U.S.C. 154(b) by 0 days.

(21) Appl. No.: 14/638,543

(22) Filed: Mar. 4, 2015

(65) Prior Publication Data

US 2015/0258069 A1   Sep. 17, 2015

Related U.S. Application Data

(60) Provisional application No. 61/952,624, filed on Mar. 13, 2014.

(51) Int. Cl.
| | | |
|---|---|---|
| A61K 31/4184 | (2006.01) |
| A61K 9/10 | (2006.01) |
| A61K 9/19 | (2006.01) |
| A61K 9/00 | (2006.01) |
| A61K 9/14 | (2006.01) |
| A61K 9/16 | (2006.01) |

(52) U.S. Cl.
CPC ........... *A61K 31/4184* (2013.01); *A61K 9/0019* (2013.01); *A61K 9/10* (2013.01); *A61K 9/145* (2013.01); *A61K 9/1623* (2013.01); *A61K 9/19* (2013.01)

(58) Field of Classification Search
CPC . A61K 9/16; A61K 31/4148; A61K 31/4184; A61K 9/0019; A61K 9/10; A61K 9/145; A61K 9/1623; A61K 9/19
See application file for complete search history.

(56) References Cited

U.S. PATENT DOCUMENTS

| | | | |
|---|---|---|---|
| 2006/0128777 A1* | 6/2006 | Bendall et al. | 514/394 |
| 2006/0159713 A1 | 7/2006 | Brittain et al. | |
| 2011/0184036 A1* | 7/2011 | Palepu | A61K 31/4184 514/394 |
| 2012/0157505 A1 | 6/2012 | LaBell et al. | |
| 2013/0210878 A1* | 8/2013 | Soppimath | A61K 47/02 614/394 |
| 2014/0142153 A1 | 5/2014 | Kocherlakota et al. | |
| 2014/0378407 A1 | 12/2014 | Khattar et al. | |

FOREIGN PATENT DOCUMENTS

| | | |
|---|---|---|
| EP | 2 641 592 | 9/2003 |
| WO | WO 2011/103150 A2 | 8/2011 |
| WO | WO 2013/102920 A1 | 7/2013 |

OTHER PUBLICATIONS

Bhawana et al. (Int J Recent Adv Pharm Res, 2012;2(2):1-16).*
Corrigan et al. (Infusion Nursing: an evidence based approach; 2011; Elsevier Health Sciences p. 416).*
Elefante et al. (AmJ Health Syst Pharm. 2010;67(9):713-723).*

(Continued)

*Primary Examiner* — Ernst V Arnold
(74) *Attorney, Agent, or Firm* — Squire Patton Boggs (US) LLP

(57) ABSTRACT

Provided herein are pharmaceutical compositions comprising nitrogen mustard, for example bendamustine hydrochloride, solid dispersions substantially free of degradants. Also provided are methods of producing and administering nitrogen mustards and in particular bendamustine hydrochloride solid dispersions substantially free of degradants. The pharmaceutical compositions can be used for any disease that is sensitive to treatment with bendamustine hydrochloride, such as neoplastic diseases.

26 Claims, 11 Drawing Sheets

(56) References Cited

OTHER PUBLICATIONS

Intravenous infusion [online] retrieved from: http://medical-dictionary.thefreedictionary.com/intravenous+infusion; Oct. 6, 2015 4 pages citing intravenous infusion. (n.d.) Miller-Keane Encyclopedia and Dictionary of Medicine, Nursing, and Allied Health, Seventh Edition. (2003).*

International Search Report mailed May 15, 2015, for PCT application No. PCT/US2015/018725, filed Mar. 4, 2015, 4 pp.
Written Opinion of the International Searching Authority mailed May 15, 2015, for PCT application No. PCT/US2015/018725, filed Mar. 4, 2015, 8 pp.

* cited by examiner

POLARIZED LIGHT MICROSCOPY FOR BATCH 1

POLARIZED LIGHT MICROSCOPY FOR BATCH 2

XPRD DIFFRACTOGRAM FOR BATCH 1

POLARIZED LIGHT MICROSCOPY FOR BATCH 3

BENDAMUSTINE SOLID DISPERSIONS AND CONTINUOUS INFUSION

CROSS-REFERENCE

The present application claims the benefit of U.S. provisional application No. 61/952,624, filed Mar. 13, 2014, the content of which is hereby incorporated by reference in its entirety.

FIELD

Provided herein are pharmaceutical compositions for the treatment of various disease states, for instance neoplastic diseases and autoimmune diseases, methods of their use, and methods of their preparation. Useful pharmaceutical compositions comprise nitrogen mustards, for instance the nitrogen mustard bendamustine, e.g., bendamustine hydrochloride.

BACKGROUND

The following description includes information that can be useful in understanding the present embodiments. It is not an admission that any such information is prior art, or relevant, to the presently claimed embodiments, or that any publication specifically or implicitly referenced is prior art.

Because of their high reactivity in aqueous solutions, nitrogen mustards can be difficult to formulate as pharmaceuticals, and they are often supplied for administration in a lyophilized form that requires reconstitution, usually in water, by skilled hospital personnel prior to administration. Once in aqueous solution, nitrogen mustards are subject to degradation by hydrolysis; thus, the reconstituted product should be administered to a patient as soon as possible after its reconstitution.

Bendamustine, 4-{5-[Bis(2-chloroethyl)amino]-1-methyl-2-benzimidazolyl}butyric acid, includes a benzimidazole ring and an active nitrogen mustard, according to Formula I.

Formula I

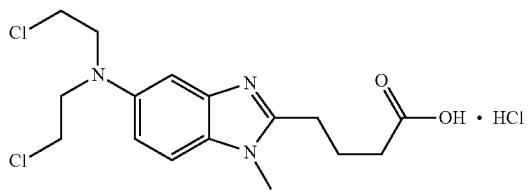

Bendamustine is also identified by the following: 5-(Bis(2-chloroethyl)amino)-1-methyl-2-benzimidazolebutyric acid; HSDB 7763; SDX-105; and UNII-9266D9P3PQ. Bendamustine is further identified by the Chemical Abstracts Service registry numbers 16506-27-7 and 3543-75-7 (hydrochloride).

Bendamustine was initially synthesized in 1963 in the German Democratic Republic (GDR) and was available from 1971 to 1992 in that location under the name Cytostasan®. Since that time, it has been marketed in Germany under the tradename Ribomustin®. It has been widely used in Germany to treat chronic lymphocytic leukemia, Hodgkin's disease, non-Hodgkin's lymphoma, multiple myeloma, and breast cancer.

Due to its degradation in aqueous solutions (like other nitrogen mustards), bendamustine is currently supplied as a lyophilized product. The current lyophilized formulations of bendamustine (Ribomustin®, Treanda®) contain bendamustine hydrochloride and mannitol in a sterile lyophilized form as a white powder for intravenous use following reconstitution. The finished lyophilisate can be unstable when exposed to light. Therefore, the product is stored in brown or amber-colored glass bottles. The current lyophilized formulations of bendamustine contain degradation products that can occur during manufacturing of the drug substance and/or during the lyophilization process to make the finished drug product.

Currently the bendamustine drug product Ribomustin® is formulated as a lyophilized powder for injection with 100 mg of drug per 50 mL vial or 25 mg of drug per 20 mL vial. The vials are opened and reconstituted as close to the time of patient administration as possible. The product is reconstituted with 40 mL (for the 100 mg presentation) or 10 mL (for the 25 mg presentation) of Sterile Water for Injection. The reconstituted product is further diluted into 500 mL, q.s., 0.9% Sodium Chloride for Injection. The route of administration is by intravenous infusion over 30 to 60 minutes.

Following reconstitution with Sterile Water for Injection, vials of Ribomustin® are stable for a period of 7 hours under room temperature storage or for 6 days upon storage at 2-8° C. The 500 mL admixture solution must be administered to the patient within 7 hours of vial reconstitution (assuming room temperature storage of the admixture).

Currently, the bendamustine drug product Treanda® is formulated as a lyophilized powder for injection with 100 mg of drug per 50 mL vial or 25 mg of drug per 20 mL vial. The vials are opened and reconstituted as close to the time of patient administration as possible. The product is reconstituted with 20 mL (for the 100 mg presentation) or 5 mL (for the 25 mg presentation) of Sterile Water for Injection. The reconstituted product is further diluted into 500 mL, q.s., 0.9% Sodium Chloride for Injection. As an alternative to 0.9% Sodium Chloride for Injection, 2.5% Dextrose/0.45% Sodium Chloride for Injection can be considered. The route of administration is by intravenous infusion over 30 to 60 minutes.

Following reconstitution with Sterile Water for Injection, vials of Treanda® are stable for a period of 3 hours under room temperature storage (15-30° C.) or for 24 hrs upon storage at 2-8° C. The 500 mL admixture solution must be administered to the patient within this period.

The reconstitution of Ribomustin® lyophilized powder is difficult. Reports from the clinic indicate that reconstitution can require at least fifteen minutes and can require as long as thirty minutes. The reconstitution of Treanda® is also difficult. Treanda®'s label indicates a 5 minute requirement for reconstitution. Besides being burdensome and time-consuming for the healthcare professional responsible for reconstituting the product, the lengthy exposure of bendamustine to water during the reconstitution process increases the potential for loss of potency and impurity formation due to the hydrolysis of the product by water.

Thus, a need exists for solid dispersions of bendamustine that are easier to reconstitute and which have a better impurity profile than the current lyophilisate (lyophilized powder) formulations of bendamustine. Also a need exists to reduce the exposure of bendamustine to water, for example during a reconstitution or infusion process, and therefore minimize or eliminate a potential loss of potency and/or impurity formation due to the hydrolysis of the compound by water.

SUMMARY

Provided herein are solid dispersions of bendamustine hydrochloride, as well as methods of their preparation. The solid dispersions of bendamustine are useful for the treatment of various disease states, for instance neoplastic diseases and autoimmune diseases.

In one aspect, provided herein solid dispersions comprising a solid form of one or more excipients, and a solid form of a nitrogen mustard compound. Useful excipients and nitrogen mustard compounds are described below. In particular embodiments, the nitrogen mustard compound is bendamustine, e.g. bendamustine hydrochloride. In particular embodiments, the excipient is mannitol.

In certain embodiments, provided herein are solid dispersions comprising a solid form of mannitol and a solid form of bendamustine hydrochloride. In certain embodiments, the solid form of mannitol is selected from the group consisting of crystalline orthorhombic polymorph α mannitol, crystalline orthorhombic polymorph β mannitol, crystalline monoclinic polymorph δ mannitol, amorphous mannitol, and combinations thereof. In certain embodiments, the bendamustine hydrochloride is selected from crystalline bendamustine hydrochloride and amorphous bendamustine hydrochloride. In certain embodiments, the bendamustine hydrochloride is selected from Form 1 bendamustine hydrochloride, Form 2 bendamustine hydrochloride, Form 3 bendamustine hydrochloride, Form 4 bendamustine hydrochloride, and mixtures thereof. In certain embodiments, the bendamustine hydrochloride is amorphous bendamustine hydrochloride. In certain embodiments, the bendamustine hydrochloride is a mixture of amorphous bendamustine hydrochloride and one or more crystalline forms of bendamustine hydrochloride. In certain embodiments, the solid dispersions are substantially free of one or more hydrolysis degradants.

In another aspect, provided herein are solid dispersions comprising a solid form of bendamustine hydrochloride and one or more pharmaceutically acceptable excipients that can be dissolved in a non-aqueous solution. In certain embodiments, the solid dispersions comprise crystalline excipient or amorphous excipient, or a combination thereof. In certain embodiments, the bendamustine hydrochloride is selected from Form 1 bendamustine hydrochloride, Form 2 bendamustine hydrochloride, Form 3 bendamustine hydrochloride, Form 4 bendamustine hydrochloride, and mixtures thereof. In certain embodiments, the bendamustine hydrochloride is amorphous bendamustine hydrochloride. In certain embodiments, the bendamustine hydrochloride is a mixture of amorphous bendamustine hydrochloride and one or more crystalline forms of bendamustine hydrochloride. In certain embodiments, the solid dispersions are substantially free of one or more hydrolysis degradants.

In another aspect, provided herein are solid dispersions comprising a nitrogen mustard compound. In certain embodiments, the nitrogen mustard compound is other than bendamustine. In certain embodiments, the compound is selected from the group consisting of cyclophosphamide, bendamustine, bisulfan, chlorambucil, carmustin, melphalan, uramustine, ifosfamide, mechlorethamine, lumustine and combinations thereof. Also provided are methods of making the solid dispersions. Such methods include, without limitation, spray drying, lyophilization, hot melt extrusion, electrospinning, super critical fluid technology, melt agglomeration, use of surfactant(s), solvent evaporation and melt evaporation. The invention teaches the use of spray drying for obtaining these solid dispersions but this can be expanded to other methods by a person skilled in the art.

In another aspect, provided herein are methods of preparing solid dispersions of nitrogen mustard compounds. Other embodiments of the description are directed to methods of preparing solid dispersions of nitrogen mustard based antineoplastic agents, other than bendamustine, with pharmaceutically acceptable excipient(s) that involve the use of a continuous pre-drying mixing, emulsification, colloid suspension followed by a continuous drying method such as spray drying, fluidized bed spray drying, continuous lyophilization. The dry powder particles obtained will be essentially free of hydrolysis degradants and exhibit desirable powder particle attributes such as chemical and physical stability and powder flowability.

Other embodiments of the description are directed to compositions comprising solid dispersions of bendamustine hydrochloride that further contain such small amounts of bendamustine degradation products so as to provide solid dispersions substantially free of degradants. As is known to persons having ordinary skill in the art, even small amounts of degradation products can have a profound impact on the solid state thermodynamics, physical properties, mechanical properties, physical and chemical stability, solubility, dissolution rate, solid state and powder morphology, particle flow properties etc.

In another aspect, provided herein are systems and methods for continuous infusion of a nitrogen mustard compound, for example bendamustine. In the methods, an intravenous solution is contacted with a solution comprising the nitrogen mustard compound. The solutions are preferably contacted at controlled flow rates. In certain embodiments, the solutions are mixed by a mixing device. In particular embodiments, a dose of the nitrogen mustard compound is delivered in 30 minutes or less. In further embodiments, also provided are compositions and apparatuses for the methods. In certain embodiments, the short contact time between the intravenous fluid and the nitrogen mustard compound solution, provided by the continuous (instead of batch) mode of operation, is capable of minimizing the creation of hydrolysis degradants of the nitrogen mustard compound. In particular embodiments, the nitrogen mustard compound is bendamustine, for example bendamustine hydrochloride.

The compositions provided herein are useful for the treatment of any condition for which a nitrogen mustard, such as bendamustine, might be effective according to the practitioner of skill. In particular embodiments, the conditions are useful for the treatment of neoplastic and/or autoimmune conditions.

DESCRIPTION OF EXEMPLARY EMBODIMENTS

Figure 1:
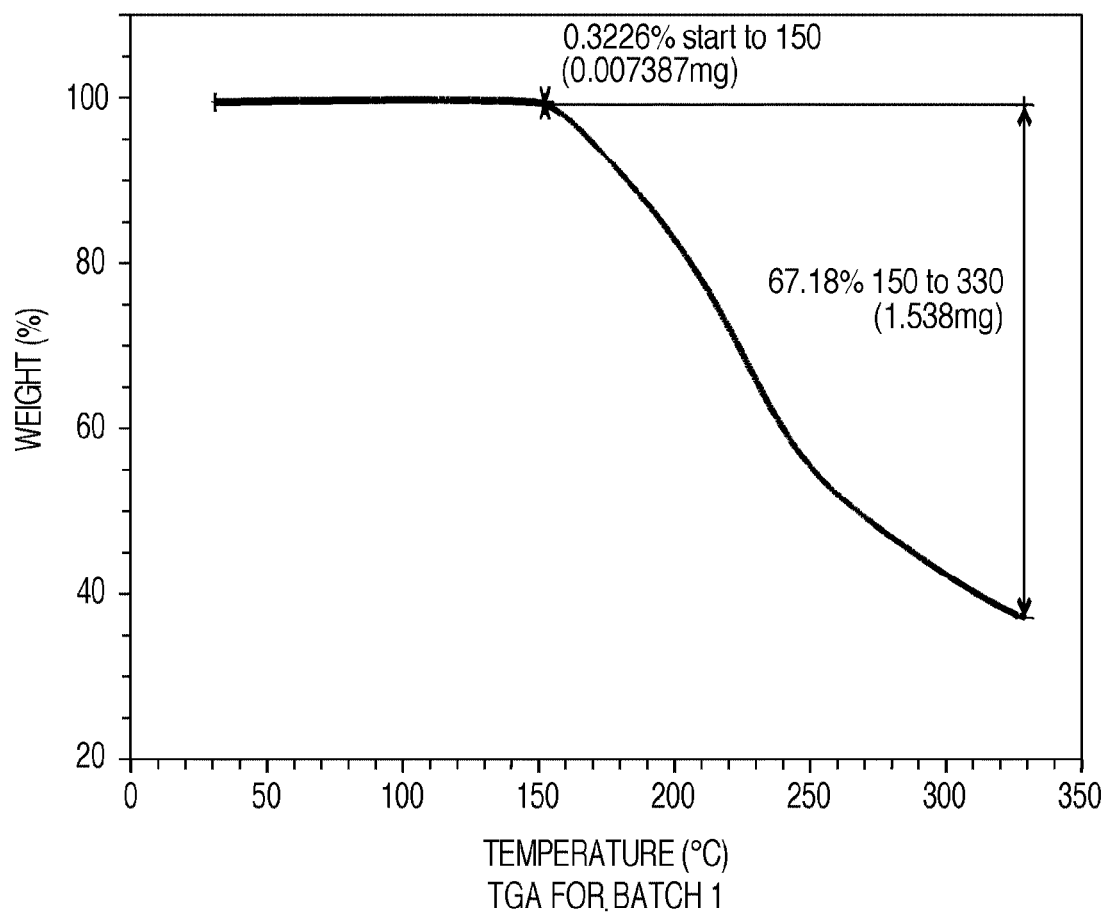
FIG. 1 provides a Thermo-Gravimetric Analysis (TGA) Thermogram of Batch 1, a solid dispersion of bendamustine hydrochloride with mannitol, substantially free of degradants. The spray dried powder has very low humidity and residual solvents.
Figure 2:
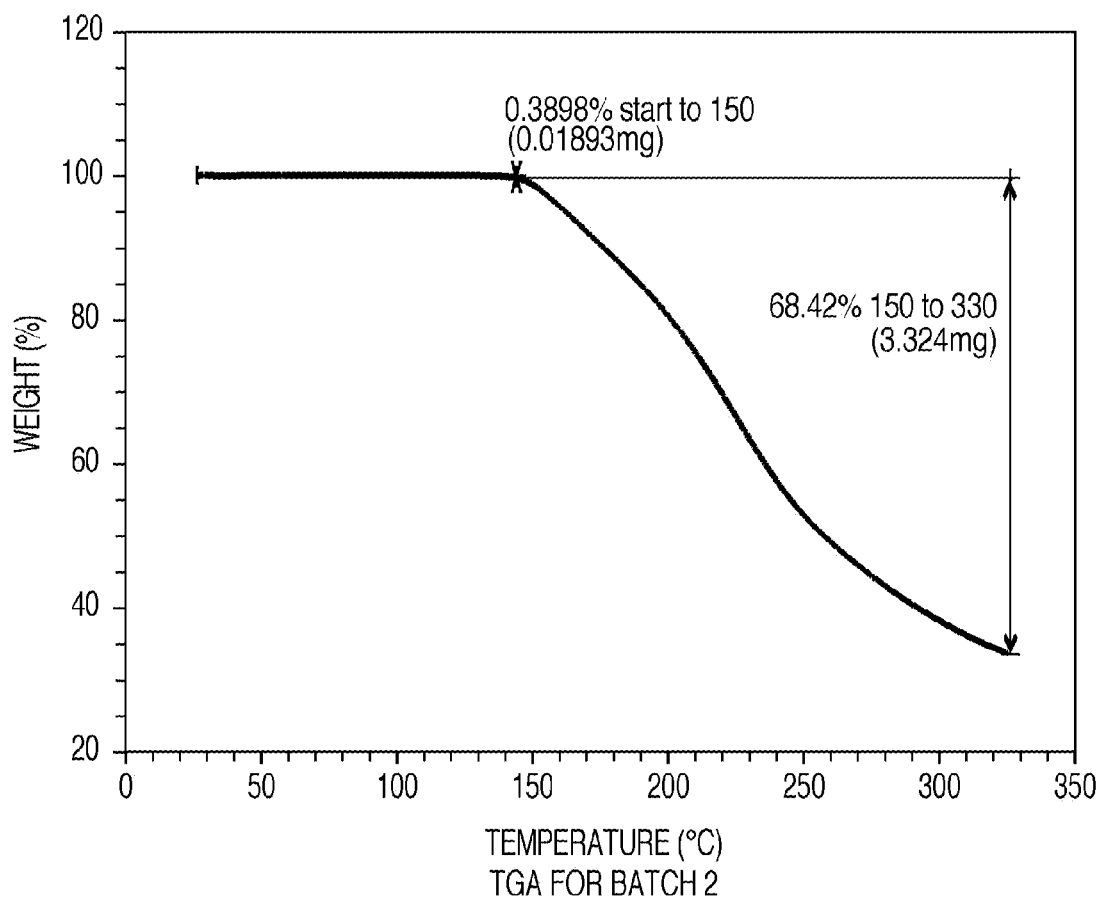
FIG. 2 provides a Thermo-Gravimetric Analysis (TGA) Thermogram of Batch 2, a solid dispersion of bendamustine hydrochloride with mannitol, substantially free of degradants. The spray dried powder has very low humidity and residual solvents.

Provided herein are compositions comprising solid dispersions of nitrogen mustard compounds, methods of their preparation and methods of their use.

Definitions

When referring to the compositions provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "solid dispersion" refers to a solid product comprising a polymeric matrix and a drug. The matrix can be either crystalline or amorphous. The drug can be dispersed molecularly, in amorphous particles, for instance clusters, or in crystalline particles. In certain embodiments, a solid dispersion is in any of the following forms, or any combination thereof: a) a simple eutectic mixture, b) a solid solution (continuous, discontinuous, substitutional, interstitial, amorphous), c) a glass solution, and d) an amorphous precipitation in a crystalline carrier. In certain embodiments, certain more complex combinations can be encountered, i.e. in the same sample some molecules are present in clusters while some are molecularly dispersed.

It is well known in persons having ordinary skill in the art of metallurgy, geology, chemistry and chemical engineering that physical, morphological, mechanical and other properties of solid dispersion can depend not only on composition but also on the method with which the dispersion is obtained (e.g., via rapid quenching from a hot melt or through cycles of aging). This is mainly due to the impact these dynamic events have on the solid lattice and surface thermodynamics of the ensuing dispersions. For instance, solid dispersions of a drug product with the same composition but obtained through different production methods, could have different solubility such that a more thermodynamically stable solid dispersion is less soluble than a less thermodynamically stable solid dispersion. Solid dispersions can also differ in properties such as shelf-life, bioavailability, morphology, density, color, and compressibility. Accordingly, variation of the characteristics of a solid dispersion of a drug product is one of many ways in which to modulate the physical and pharmacological properties thereof.

The term "crystalline," as used herein, means having a regularly repeating arrangement of molecules or external face planes.

The term "crystalline composition," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, and desolvated solvates.

The term "pharmaceutically acceptable excipient," as used herein, includes any and all solvents, dispersion media, coatings, antibacterial and antifungal agents, isotonic and absorption delaying agents and the like. The use of such media and agents for pharmaceutical active substances is well known in the art, such as in *Remington: The Science and Practice of*

*Pharmacy*, 20<sup>th</sup> ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

The term "solution" as used herein, refers to a mixture containing at least one solvent and at least one compound that is at least partially dissolved in the solvent. The term "solvate," as used herein, means a crystalline composition of variable stoichiometry formed by a solute and an organic solvent as defined herein.

The term "continuous mode of operation" as used herein, refers to a mode of operating a system and/or apparatus where the in-flow into and the out-flow from the system/apparatus are of non-zero value within a specified period of time. For example, "continuous mixer" may refer to an apparatus defined between two continuously operating pump(s) which are feeding two distinct in-flows into the mixer for the purpose of mixing/combining them and a continuous spray drier which receives the combined out-flow from the mixer. The "continuous mode of operation" is distinct from a "batch mode of operation" which within the same timeframe is characterized by intermittent operation of the in-flows into and out-flows from the system/apparatus. For example, "batch mixer" may refer to an apparatus defined between two non-continuously operating pumps which first feed the two distinct in-flows to a vessel, then stop and allow mixing to occur (e.g. via stirring). Once mixing is accomplished, the out-flow from the mixing vessel (which thus far was maintained a value of zero) assumes a non-zero value and empties the contents of the vessel into a spray drier. One major difference between the two distinct mode of operations is that while they may attain the same result regarding mixing efficiency, the overall contact time between the two combined in-flow streams is significantly smaller in a continuous mode of operation. For an intravenous infusion with mixing, a "continuous mode of operation" indicates that there is a constant flow of at least two solutions into a mixing chamber, and the resulting mixed stream is for administration to a patient.

The term "emulsion" as used herein, refers to a mixture of two liquids that are normally immiscible or exhibit very low miscibility. Such emulsions can be obtained, for example, by mixing water with water immiscible solvents like perfluorohexane, perfluorooctane, perflenapent, hexafluorobenzene, or perfluoromethylcyclohexane.

The term "solvent" as used herein, means a substance, typically a liquid, that is capable of completely or partially dissolving another substance, typically a solid. Useful solvents include, but are not limited to, water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone (butanone), 1-methyl-2-pyrrolidinone, mesitylene, nitromethane, polyethylene glycol, propanol, 2-propanone, propionitrile, pyridine, tetrahydrofuran, toluene, xylene, perfluorohaxane, perflenapent, hexafluorobenzene, perfluoromethylcyclohexane, Fluorinert, perfluorooctane, tertbutylmethylether, ethyl ether, ethyl formate, isopropyl acetate, propyl acetate, mixtures thereof and the like.

The term "substantially free," as used herein with regard to compositions that contain a particular form of bendamustine hydrochloride while being "substantially free" of other forms of the compound, means that the recited form is associated with less than 10%, preferably less than 5%, in particular less than 2% and most preferably less than 1% of the other recited forms of bendamustine hydrochloride. The term "substantially free," as used herein with regard to compositions that contain bendamustine hydrochloride while being "substantially free" of degradants of the compound, means that the recited form is associated with less than 2%, preferably less than 1%, more preferably less than 0.5%, in particular less than 0.1% and most preferably less than 0.05% of the degradants of bendamustine hydrochloride in aqueous and non-aqueous solutions.

The term "spray drying or equivalent" as used herein, refers to a drying unit operation consisting of a solution introduced continuously or intermittently into a drying chamber. The solution is usually, but not exclusively, introduced through one or more spray nozzles located usually, but not exclusively either on the top or the bottom of the drying chamber. The droplets of the solution are dried by means of heat, mass or momentum gradients within the chamber. These gradients are provided either by a process gas stream of elevated temperature and/or particles in a fluidized bed form. The particles formed by drying the solution droplets may or may not be recycled back into the drying chamber in order to obtain specific particle characteristics or level of dryness. The operating pressure of the drying chamber can be above, at or below atmospheric pressure. As a result, the operating temperature profile inside the drying chamber could range (in case of water based solutions) from above 100° C. (for operating temperatures above 1 atm) to less than 0° C. (for high vacuums).

The term "therapeutically effective amount" as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

The term "degradant" as used herein, refers to products of chemical side reactions of bendamustine obtained during the preparation of pharmaceutical compositions comprising bendamustine. These include, but are not limited to, products of hydrolysis of bendamustine.

The term "HP1" refers to a compound of formula II:

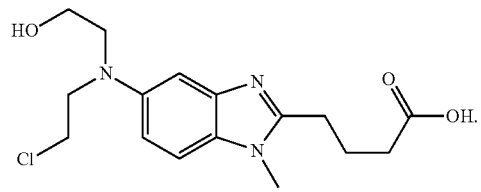

Formula II

The term "bendamustine dimer" refers to a compound of Formula III:

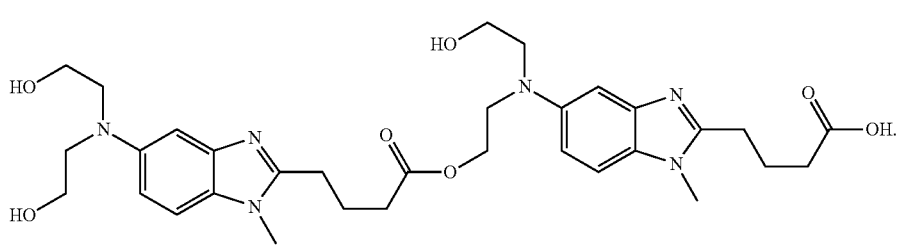

Formula III

The terms "bendamustine ethyl ester" and "BM1EE" refer to a compound of Formula IV:

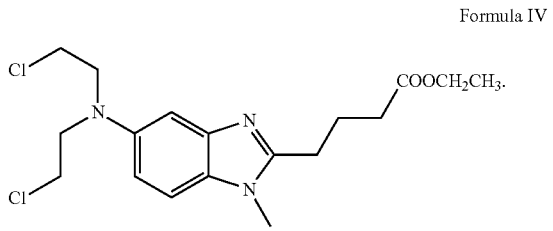

Formula IV

The terms "des-chloroethyl bendamustine" and "BM1DCE" refer to a compound of Formula V:

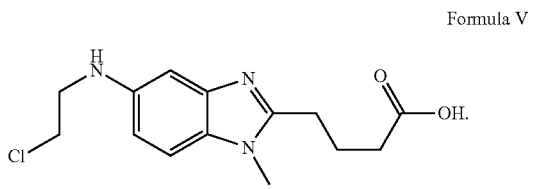 [SMILES: Cn1c(CCCC(=O)O)nc2cc(NCCCl)ccc21]

Formula V

The term "HP2" refers to a compound of Formula VI.

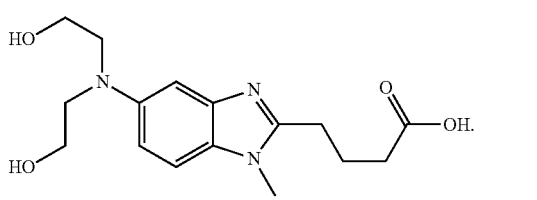

Formula VI

The term "bendamustine crystalline polymorph form 1" (Form 1) refers to a crystalline polymorph of bendamustine that exhibit reflections on an XRPD diffractogram at at least two, three, or four of 8.3, 14, 16.8, 18.5±0.2 degrees 2θ.

The term "bendamustine crystalline polymorph form 2" (Form 2) refers to a crystalline polymorph of bendamustine that exhibit reflections on an XRPD diffractogram at at least two, three, or four of 10.6, 15.1, 18.9, 23.1±0.2 degrees 2θ.

The term "bendamustine crystalline polymorph form 3" (Form 3) refers to a crystalline polymorph of bendamustine that exhibit reflections on an XRPD diffractogram at at least two, three, or four of 7.9, 10.6, 15.5, 19.7±0.2 degrees 2θ.

The term "bendamustine crystalline polymorph form 4" (Form 4) refers to a crystalline polymorph of bendamustine that exhibit reflections on an XRPD diffractogram at at least two, three, or four of 10.8, 15.5, 19.6 and 23.5±0.2 degrees 2θ.

The term "about" refers to a tolerance above and below a particular value. Those of skill will recognize that a range about a value encompasses those numeric amounts that do not deviate substantially from that value. In certain embodiments, the term "about" refers to a range that encompasses one standard deviation from a value. In certain embodiments, the term "about" refers to a range that encompasses ±2% of a value. In certain embodiments, the term "about" refers to a range that encompasses ±1% of a value. In certain embodiments, the term "about" refers to a range that encompasses ±2 units after the last significant digit of the value. For instance, "about 1.5" can refer to 1.5±0.02. In certain embodiments, the term "about" refers to a range that encompasses ±1 units after the last significant digit of the value. For instance, "about 1.5" can refer to 1.5±0.01.

Compositions

Provided herein are solid dispersions of bendamustine hydrochloride with pharmaceutically acceptable excipients. Spectral and microscopy data relating to these solid dispersions of bendamustine hydrochloride are depicted in FIGS. 1-9, and methods of preparing each of these forms are provided.

In one aspect, provided herein solid dispersions comprising a solid form of one or more excipients, and a solid form of a nitrogen mustard compound. Useful excipients and nitrogen mustard compounds are described below. In particular embodiments, the nitrogen mustard compound is bendamustine, e.g. bendamustine hydrochloride. In particular embodiments, the excipient is mannitol.

In one aspect, provided herein are solid dispersions comprising one or more crystalline or amorphous form(s) of mannitol and one or more crystalline or amorphous form(s) of a nitrogen mustard compound. The nitrogen mustard compound can be any nitrogen mustard compound known to those of skill. In certain embodiments, the nitrogen mustard compound is selected from the group consisting of bendamustine, cyclophosphamide, bisulfan, chlorambucil, carmustin, melphalan, uramustine, ifosfamide, mechlorethamine, lumustine and salts and combinations thereof. In certain embodiments, the nitrogen mustard compound is other than bendamustine. In certain embodiments, the nitrogen mustard compound is selected from the group consisting of cyclophosphamide, bisulfan, chlorambucil, carmustin, melphalan, uramustine, ifosfamide, mechlorethamine, lumustine and salts and combinations thereof.

In certain embodiments, the nitrogen mustard compound is bendamustine. The bendamustine can be any form of bendamustine known to those of skill in the art. In certain embodiments, the bendamustine is a pharmaceutically acceptable salt of bendamustine. In certain embodiments, the bendamustine is bendamustine hydrochloride. In certain embodiments, the bendamustine hydrochloride is amorphous. In certain embodiments, the bendamustine hydrochloride is amorphous and substantially free of crystalline bendamustine hydrochloride.

In certain embodiments, bendamustine hydrochloride is in a crystalline form selected from Form 1 bendamustine hydrochloride, Form 2 bendamustine hydrochloride, Form 3 bendamustine hydrochloride, Form 4 bendamustine hydrochloride, and mixtures thereof. In certain embodiments, the crystalline form is substantially free of amorphous bendamustine hydrochloride. In certain embodiments, the crystalline form is mixed with amorphous bendamustine hydrochloride.

Any of the solid forms of bendamustine hydrochloride can be a component of a composition comprising bendamustine hydrochloride. In some embodiments, these compositions comprising at least one of the solid forms of bendamustine hydrochloride described herein are substantially free of other solid forms of bendamustine hydrochloride.

In certain embodiments, the solid dispersions comprise bendamustine and are substantially free of bendamustine crystalline forms that exhibit XRPD peaks at 8.3, 14, 16.8, 18.5±0.2 degrees 2θ or peaks at 7.9, 10.6, 15.5, 19.7±0.2 degrees 2θ. In certain embodiments, the solid dispersions comprise amorphous bendamustine and are substantially free of bendamustine crystalline forms that exhibit XRPD peaks at 8.3, 14, 16.8, 18.5±0.2 degrees 2θ or peaks at 7.9, 10.6, 15.5, 19.7±0.2 degrees 2θ.

In certain embodiments, the solid dispersions comprise bendamustine hydrochloride and are substantially free of bendamustine crystalline forms that exhibit XRPD peaks at any one, two, three, or four of 8.3, 14, 16.8, and 18.5±0.2 degrees 2θ. In certain embodiments, the solid dispersions comprise bendamustine hydrochloride and are substantially free of bendamustine crystalline forms that exhibit XRPD peaks at any one, two, three, four, five, six, seven, or eight of 8.3, 14, 16.8, 18.5, 22, 22.9, 25.1 and 28.3±0.2 degrees 2θ. In certain embodiments, the solid dispersions comprise amorphous bendamustine and are substantially free of bendamustine crystalline forms that exhibit XRPD peaks at any one, two, three, or four of 7.9, 10.6, 15.5, and 19.7±0.2 degrees 2θ. In certain embodiments, the solid dispersions comprise amorphous bendamustine and are substantially free of bendamustine crystalline forms that exhibit XRPD peaks at any one, two, three, four, five, or six of 7.9, 10.6, 15.5, 19.7, 23.3 and 26.1±0.2 degrees 2θ. In certain embodiments, the solid dispersions comprise amorphous bendamustine and are substantially free of bendamustine crystalline forms that exhibit XRPD peaks at any one, two, three, four, five, or six of 10.2, 10.6, 13.7, 15.1, 23.1, and 23.4±0.2 degrees 2θ. In certain embodiments, the solid dispersions comprise amorphous bendamustine and are substantially free of bendamustine crystalline forms that exhibit XRPD peaks at any one, two, three, four, or five of 10.3, 10.8, 15.5, 19.6, and 23.5±0.2 degrees 2θ.

In certain embodiments, the solid dispersions comprise bendamustine hydrochloride and are substantially free of bendamustine crystalline forms that exhibit XRPD peaks at any one, two, three, four or five of 25.12, 24.85, 22.92, 21.97, and 14.05±0.2 degrees 2θ. In certain embodiments, the solid dispersions comprise bendamustine hydrochloride and are substantially free of bendamustine crystalline forms that exhibit further XRPD peaks at any one, two, three, four, or five of 16.82, 17.51, 18.45, 24.85, and 28.33±0.2 degrees 2θ.

In certain embodiments, the solid dispersions comprise amorphous bendamustine and are substantially free of bendamustine crystalline forms that exhibit XRPD peaks at any one, two, or three of 10.64, 20.12, and 20.45±0.2 degrees 2θ. In certain embodiments, the solid dispersions comprise amorphous bendamustine and are substantially free of bendamustine crystalline forms that exhibit further XRPD peaks at any one, two, three, four, five, six, or seven of 10.17, 15.06, 18.82, 20.95, 25.20, 26.54, and 29.05±0.2 degrees 2θ.

In certain embodiments, the solid dispersions comprise bendamustine hydrochloride and are substantially free of bendamustine crystalline forms that exhibit XRPD peaks at any one, two, or three of 26.08, 27.85, and 28.11±0.2 degrees 2θ. In certain embodiments, the solid dispersions comprise bendamustine hydrochloride and are substantially free of bendamustine crystalline forms that exhibit further XRPD peaks at any one, two, or three of 10.58, 15.55, and 19.75±0.2 degrees 2θ.

In certain embodiments, the solid dispersions comprise amorphous bendamustine and are substantially free of bendamustine crystalline forms that exhibit XRPD peaks at any one, two, three, or four of 10.83, 15.52, 20.45, and 23.58±0.2 degrees 2θ. In certain embodiments, the solid dispersions comprise amorphous bendamustine and are substantially free of bendamustine crystalline forms that exhibit further XRPD peaks at any one, two, three, four, five, or six of 10.27, 19.64, 20.73, 21.23, 25.81, and 27.63±0.2 degrees 2θ.

In particular embodiments, the solid dispersion comprises one or more pharmaceutically acceptable excipients, diluents or carriers in solid form. Those of skill in the art will recognize that suitable excipients, diluents, and carriers can be dried to a solid form according to the methods below.

The excipient can be in any amount deemed useful to the practitioner of skill. In particular embodiments, the ratio of nitrogen mustard compound to excipient is from about 1:1.0 to about 1:2.0. In particular embodiments, the ratio of nitrogen mustard compound to excipient is about 1:1.1. In particular embodiments, the ratio of nitrogen mustard compound to excipient is about 1:1.2. In particular embodiments, the ratio of nitrogen mustard compound to excipient is about 1:1.3. In particular embodiments, the ratio of nitrogen mustard compound to excipient is about 1:1.4. In particular embodiments, the ratio of nitrogen mustard compound to excipient is about 1:1.5. In particular embodiments, the ratio of nitrogen mustard compound to excipient is about 1:1.6. In particular embodiments, the ratio of nitrogen mustard compound to excipient is about 1:1.7. In particular embodiments, the ratio of nitrogen mustard compound to excipient is about 1:1.8. In particular embodiments, the ratio of nitrogen mustard compound to excipient is about 1:2.0.

In certain embodiments, provided herein are pharmaceutical compositions that further comprise at least one pharmaceutically acceptable excipient. Preferred excipients include, for example, sodium phosphate, potassium phosphate, sodium chloride, citric acid, tartaric acid, gelatin, glycine, mannitol, lactose, sucrose, maltose, glycerin, dextrose, dextran, trehalose, hetastarch, polyvinylpyrrolidone, polyethylene glycols, polymethacrylates, hydroxypropylmethylcellulose, hydroxypropylmethylcellulose acetate succinate, ethylcellulose, hydroxypropylcellulose cyclodextrins or a mixture thereof. More preferred pharmaceutical excipients are mannitol, polyvinylpyrrolidone, hydroxypropylmethylcellulose acetate succinate.

In certain embodiments, the solid dispersion comprises a saccharide excipient or a saccharide alcohol excipient. In certain embodiments, the excipient is selected from the group consisting of mannitol, maltitol, sorbitol, erythritol, xylitol, lactitol, lactose, sucrose, glycose, maltose, trehalose, dextrose, and combinations thereof. In particular embodiments, the excipient is mannitol. In particular embodiments, the excipient is mannitol and the nitrogen mustard compound is bendamustine hydrochloride.

In particular embodiments, the ratio of bendamustine hydrochloride to mannitol is from about 1:1.0 to about 1:2.0. In particular embodiments, the ratio of bendamustine hydrochloride to mannitol is about 1:1.1. In particular embodiments, the ratio of bendamustine hydrochloride to mannitol is about 1:1.2. In particular embodiments, the ratio of bendamustine hydrochloride to mannitol is about 1:1.3. In particular embodiments, the ratio of bendamustine hydrochloride to mannitol is about 1:1.4. In particular embodiments, the ratio of bendamustine hydrochloride to mannitol is about 1:1.5. In particular embodiments, the ratio of bendamustine hydrochloride to mannitol is about 1:1.6. In particular embodiments, the ratio of bendamustine hydrochloride to mannitol is about 1:1.7. In particular embodiments, the ratio of bendamustine hydrochloride to mannitol is about 1:1.8. In particular embodiments, the ratio of bendamustine hydrochloride to mannitol is about 1:2.0.

The mannitol can be in any form known to those of skill in the art. In particular embodiments, the mannitol is in a form selected from the group consisting of crystalline orthorhombic polymorph α mannitol, crystalline orthorhombic polymorph β mannitol, crystalline monoclinic polymorph δ mannitol, amorphous mannitol, and combinations thereof. In particular embodiments, the mannitol is amorphous. In further embodiments, the mannitol is in a crystalline form. In further embodiments, the mannitol is a mixture of crystalline and amorphous forms.

In certain embodiments, the excipient is a polymer excipient. In particular embodiments, the excipient is selected from the group consisting of vinylpyrrolidone, hydroxypropyl methyl cellulose, hydroxypropyl methyl cellulose acetate succinate (HPMC-AS), ethylene glycol, propylene glycol, propylene carbonate, vinyl acetate, vinyl propionate, vinyl caprolactame, cellulose acetate, ethyl cellulose, methyl methacrylate, methacrylic acid, polymers and co-polymers thereof.

In certain embodiments, the solid dispersion further comprises a solvent. Solvents provided herein include water and organic solvents that form stable solutions with bendamustine hydrochloride without appreciably degrading the bendamustine during the manufacturing process, and which are capable of being essentially completely evaporated through drying. In certain embodiments such solvents can be water miscible.

In certain embodiments, the solid dispersion further comprises a non-aqueous water immiscible solvent. In particular embodiments, the excipient is selected from the group consisting of perfluorohexane, perflenapent, hexafluorobenzene, perfluoromethylcyclohexane, Fluorinert, perfluorooctane and mixtures thereof.

In certain embodiments, the solid dispersion further comprises a non-aqueous water miscible or a non-aqueous partially water miscible solvent. Examples of suitable water miscible organic solvents include methanol, ethanol, n-propanol, iso-propanol, n-butanol, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, dimethyl acetamide, hexafluoroacetone, chlorobutanol, dimethyl sulfone, acetic acid, cyclohexane, n-methyl-2-pyrrolidone (NMP), dimethylformamide (DMF), and mixtures thereof. Examples of suitable organic solvents that are partially water miscible are tertbutylmethylether, ethyl ether, ethyl formate, isopropyl acetate, toluene, methyl ethyl ketone, and propyl acetate. In particular embodiments, the excipient is selected from the group consisting of methanol, ethanol, n-propanol, iso-propanol, n-butanol, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, dimethyl acetamide, hexafluoroacetone, chlorobutanol, dimethyl sulfone, acetic acid, cyclohexane, n-methyl-2-pyrrolidone (NMP), dimethylformamide (DMF), tertbutylmethylether, ethyl ether, ethyl formate, isopropyl acetate, toluene, methyl ethyl ketone, propyl acetate, and a mixture thereof.

A preferred organic solvent is ethanol. Another preferred organic solvent is perfluorohexane or perfluorooctane. Another preferred organic solvent is n-propanol. Another preferred organic solvent is NMP or DMSO.

Figure 3:
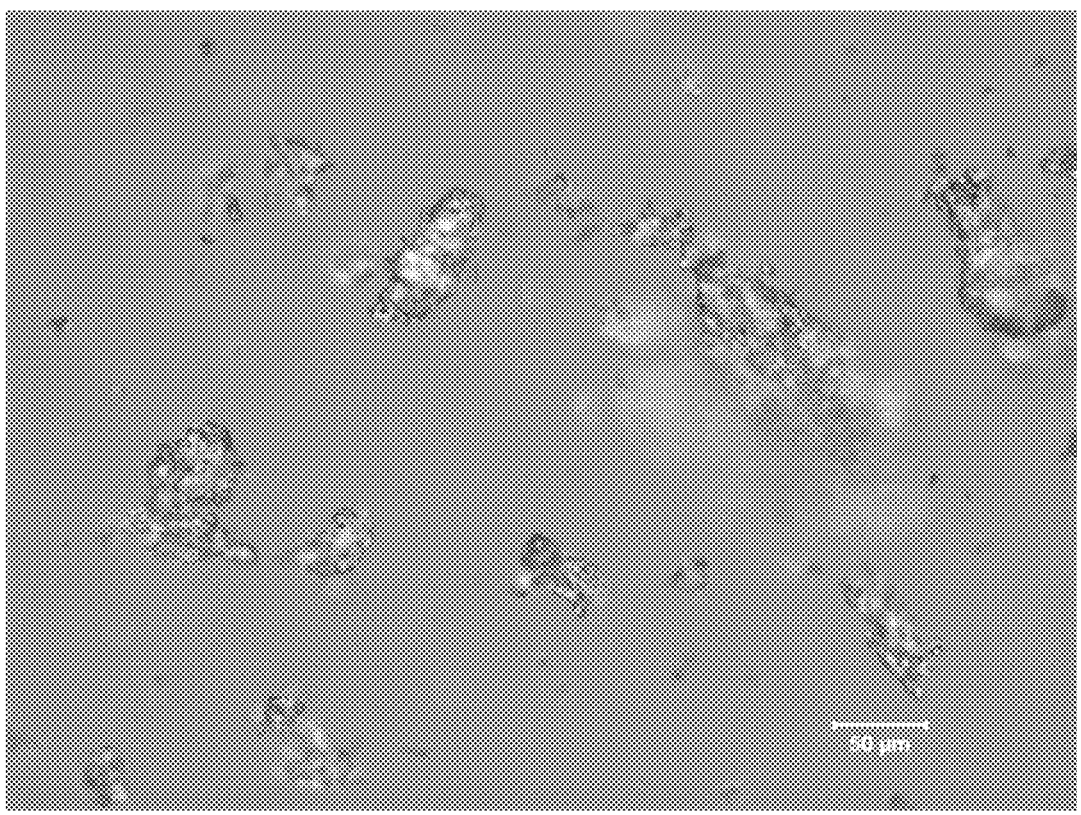
FIG. 3 provides a Polarized Light Microscopy image of particles from Batch 1, a solid dispersion of bendamustine hydrochloride with mannitol, substantially free of degradants.
Figure 4:
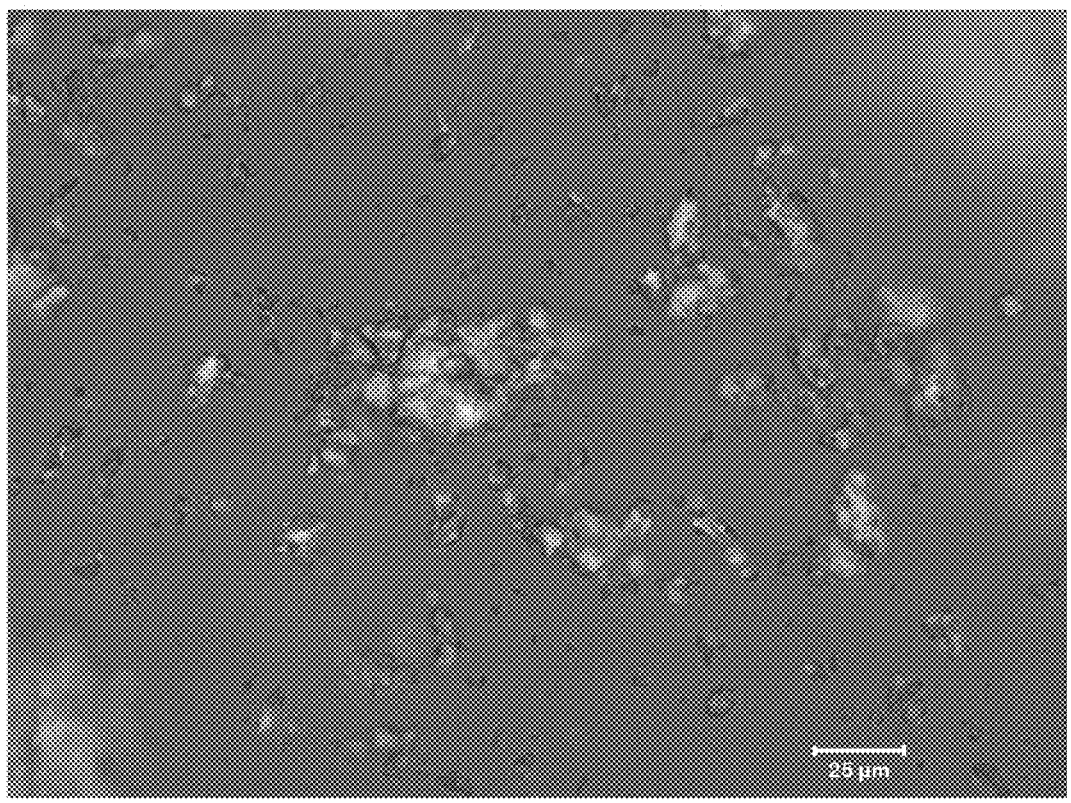
FIG. 4 provides a Polarized Light Microscopy image of particles from Batch 2, a solid dispersion of bendamustine hydrochloride with mannitol, substantially free of degradants.
Figure 7:
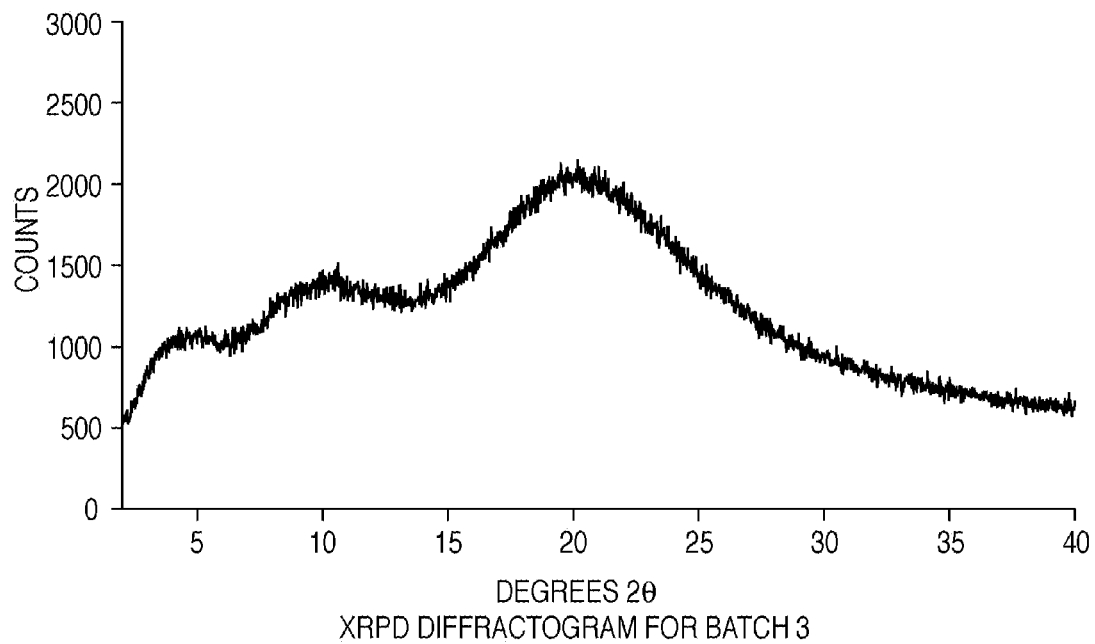
FIG. 7 provides an X-ray Powder Diffractogram (XRPD) of Batch 3, a solid dispersion of bendamustine hydrochloride with PVP, substantially free of degradants.
Figure 9:
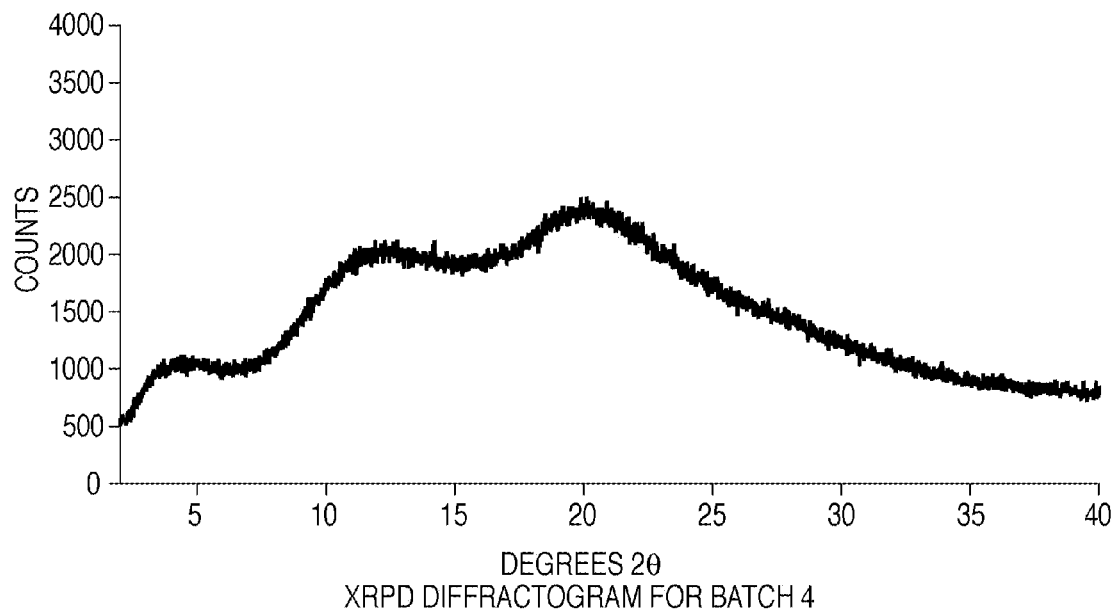
FIG. 9 provides an X-ray Powder Diffractogram (XRPD) of Batch 4, a solid dispersion of bendamustine hydrochloride with HPMC/AS, substantially free of degradants.

Preferred additives are mannitol, polyvinylpyrrolidone, hydroxypropylmethylcellulose acetate succinate. An even more preferred pharmaceutical excipient is mannitol. A preferred spray drying composition provided herein comprises a mixture of amorphous bendamustine hydrochloride, one or more bendamustine hydrochloride crystalline forms and at least one pharmaceutically acceptable excipient that is preferably mannitol An even more preferred spray drying composition provided herein comprises a mixture of amorphous bendamustine hydrochloride, no bendamustine hydrochloride crystalline form of the polymorphs Form 1 and Form 3, and at least one pharmaceutically acceptable excipient that is preferably mannitol (See, FIGS. 1-5 and Table 4-5). Another preferred spray drying composition provided herein comprises a mixture of amorphous bendamustine hydrochloride and at least one pharmaceutically acceptable excipient that is preferably polyvinylpyrrolidone or hydroxypropylmethylcellulose acetate succinate (See, e.g. FIG. 7-9). The solid dispersion of bendamustine hydrochloride with mannitol was characterized as a white powder with good flow characteristics consisting of elongated particles. (FIGS. 3-4). These good flow characteristics enable the accurate dispensing of pharmaceutical doses in the appropriate containers. The solid dispersion of bendamustine hydrochloride with polyvinylpyrrolidone was characterized as a white powder comprising amorphous polyvinylpyrrolidone and bendamustine as revealed by its diffractogram (FIG. 7). The solid dispersion of bendamustine hydrochloride with hydroxypropylmethylcellulose acetate succinate was characterized as a white powder comprising amorphous hydroxypropylmethylcellulose acetate succinate and bendamustine as revealed by its diffractogram (FIG. 9).

In advantageous embodiments, the solid dispersions are substantially free of degradants. In other advantageous embodiments, the solid dispersions are substantially free of hydrolysis degradants. Degradants include hydrolysis degradants of any component of the solid dispersion. In particular embodiments, the degradants are hydrolysis degradants of the nitrogen mustard compound. In particular embodiments, the degradants are degradants of bendamustine. In particular embodiments, the degradants are selected from the group consisting of HP1, bendamustine dimer, bendamustine ethyl ester (BM1EE), des-chloroethyl bendamustine (BM1DCE), HP2, and salts, combinations and multimers thereof. In certain embodiments, the solid dispersions comprise less than 3.5 or 3.0 or 2.5% total bendamustine degradation products, other than hydrolysis degradants, relative to bendamustine In certain embodiments, the solid dispersions comprise a nitrogen mustard compound uniformly dispersed in excipient. By "uniformly dispersed" is meant that the solid dispersion complies with the dose uniformity guidelines USP (905), the contents of which are hereby incorporated by reference. In certain embodiments, the dispersions comprise a bendamustine uniformly dispersed in excipient. In certain embodiments, the dispersions comprise a bendamustine hydrochloride uniformly dispersed in excipient. In certain embodiments, the dispersions comprise a bendamustine hydrochloride uniformly dispersed in mannitol. In certain embodiments, the dispersions comprise a bendamustine hydrochloride uniformly dispersed in crystalline mannitol. In certain embodiments, the dispersions comprise a bendamustine hydrochloride uniformly dispersed in crystalline and amorphous mannitol. In certain embodiments, the dispersions comprise a bendamustine hydrochloride uniformly dispersed in amorphous polymeric excipient. In certain embodiments, the dispersions comprise a bendamustine hydrochloride uniformly dispersed in amorphous polyvinylpyrrolidone or amorphous hydroxypropylmethylcellulose acetate succinate.

In certain embodiments, the solid dispersions comprise a trace amount of a solvent. The trace amount of the solvent can be the residue of a preparation step. In certain embodiments, the trace amount is less than 0.5%, less than 0.4%, less than 0.3%, less than 0.2%, or less than 0.1%. In particular embodiments, the solid dispersions comprise a trace amount of water, ethanol, N-methyl-pyrrolidone, n-propanol, or perfluorohexane.

In certain embodiments, the solid dispersions comprise bendamustine hydrochloride and mannitol, in a ratio of about 1:1.2, and a trace amount of N-methyl-pyrrolidone or dimethylsulfoxane. In certain embodiments, the solid dispersions comprise bendamustine hydrochloride and mannitol, in a ratio of about 1:1.7, and a trace amount of N-methyl-pyrrolidone or dimethylsulfoxane. In certain embodiments, the solid dispersions comprise bendamustine hydrochloride and mannitol, in a ratio of about 1:1.8, and a trace amount of N-methyl-pyrrolidone or dimethylsulfoxane In certain embodiments, the solid dispersions comprise bendamustine hydrochloride and mannitol, in a ratio of about 1:1.2, and a trace amount of n-propanol. In certain embodiments, the solid dispersions comprise bendamustine hydrochloride and mannitol, in a ratio of about 1:1.7, and a trace amount of n-propanol. In certain embodiments, the solid dispersions comprise bendamustine hydrochloride and mannitol, in a ratio of about 1:1.8, and a trace amount of n-propanol.

In certain embodiments, the solid dispersions comprise bendamustine hydrochloride and mannitol, in a ratio of about 1:1.2, and a trace amount of perfluorohexane or perfluorooctane. In certain embodiments, the solid dispersions comprise bendamustine hydrochloride and mannitol, in a ratio of about 1:1.7, and a trace amount of perfluorohexane or perfluorooctane. In certain embodiments, the solid dispersions comprise bendamustine hydrochloride and mannitol, in a ratio of about 1:1.8, and a trace amount of perfluorohexane or perfluorooctane.

In certain embodiments, provided herein are pharmaceutical compositions comprising any solid dispersion described herein. The pharmaceutical compositions can comprise a solid dispersion and one or more pharmaceutically acceptable diluents, excipients, or carriers. The diluents, excipients, or carriers can be in any form deemed suitable including dry, dried, solid, gel, etc. These pharmaceutical compositions may be prepared as injectables, either as liquid solutions or suspensions, as well as solid forms, for example, capsules, tablets, lozenges, pastilles, powders, suspensions, and the like.

In certain embodiments, provided herein are pharmaceutical dosage forms comprising any solid form or pharmaceutical composition provided herein. The pharmaceutical dosage form can comprise an amount of active nitrogen mustard compound to provide a single dose or multiple doses of the active nitrogen mustard compound to a patient in need thereof. In certain embodiments, the dosage form can be about 1 to about 1000 mg, about 5 to about 500 mg of nitrogen mustard compound, about 10 to about 200 mg of nitrogen mustard compound, about 25 mg of nitrogen mustard compound, about 100 mg of nitrogen mustard compound, or about 200 mg of nitrogen mustard compound. In particular embodiments, the dosage forms have the purity and/or stability described herein. In further embodiments, the pharmaceutical dosage forms comprise integer multiples of one of the above amounts. In certain embodiments, the dosage form can be reconstituted into a pharmaceutically acceptable injectable form within 5, 4, 3, 2, or 1 minutes. In certain embodiments, the dosage form is an oral dosage form.

In particular embodiments, the nitrogen mustard compound of the dosage form is bendamustine, e.g. bendamustine hydrochloride. In particular embodiments, the dosage form comprises bendamustine hydrochloride and mannitol in a ratio of about 1:1.2. In particular embodiments, the dosage form comprises bendamustine hydrochloride and mannitol in a ratio of about 1:1.3. In particular embodiments, the dosage form comprises bendamustine hydrochloride and mannitol in a ratio of about 1:1.4. In particular embodiments, the dosage form comprises bendamustine hydrochloride and mannitol in a ratio of about 1:1.5. In particular embodiments, the dosage form comprises bendamustine hydrochloride and mannitol in a ratio of about 1:1.6. In particular embodiments, the dosage form comprises bendamustine hydrochloride and mannitol in a ratio of about 1:1.7. In particular embodiments, the dosage form comprises bendamustine hydrochloride and mannitol in a ratio of about 1:1.8. In particular embodiments, the dosage form comprises bendamustine hydrochloride and mannitol in a ratio of about 1:2.

In certain embodiments, provided herein are pharmaceutical compositions comprising a pharmaceutically acceptable infusion diluent as referenced herein, a pharmaceutically acceptable reconstitution solvent as referenced herein (including WFI), a pharmaceutically acceptable additive or excipient as referenced herein, a pharmaceutically acceptable pre-drying non-aqueous solvent as referenced herein and bendamustine hydrochloride with a bendamustine concentration of 0.2, 0.3, 0.4, 0.6, 0.8, 1.0, 1.5, 2.0, 2.5, 3.0, 4.0 mg/ml that is substantially free of hydrolysis degradants. In particular embodiments, provided herein are pharmaceutical compositions comprising 0.9% Sodium Chloride infusion diluent, dimethylsulfoxide reconstitution solvent, mannitol, n-propanol and bendamustine hydrochloride with a bendamustine concentration of about 0.25, 0.32, 0.5, 0.6, 1.0, 1.5, 2.0, 4.0 mg/ml that is substantially free of hydrolysis degradants. In particular embodiments, provided herein are pharmaceutical compositions comprising of 0.9% Sodium Chloride infusion diluent, ethanol as reconstitution and pre-drying solvent, PVP and bendamustine hydrochloride with a bendamustine concentration of about 0.2, 0.25, 0.35, 0.5, 0.6, 1.0, 1.5, 2.0, 4.0 mg/ml that is substantially free of hydrolysis degradants.

Analysis

Certain of embodiments may be characterized, at least in part, by X-ray Powder Diffraction. As is known in the art, crystalline solids produce a distinctive diffraction pattern of peaks, represented in what is referred to as a diffractogram. The peak assignments for a given crystalline material, for example, degree 2Θ values, may vary slightly, depending on the instrumentation used to obtain the diffractogram and certain other factors, for example, sample preparation. Nevertheless, these variations should not be more than +/−0.2 degrees 2Θ and the relative spacing between the peaks in the diffractogram should be the same, regardless of the instrumentation used or the method of sample preparation, and the like. In particular embodiments, the solid dispersions are characterized by XRPD on a Rigaku Smart-Lab X-ray diffraction system using an incident beam of Cu Kα radiation produced using a long fine focus source that was operated at 40 kV and 44 mA, or a PANalytical X'Pert PRO MPD diffractometer using an incident beam of Cu Kα radiation produced using a long, fine-focus source and a nickel filter.

Figure 5:
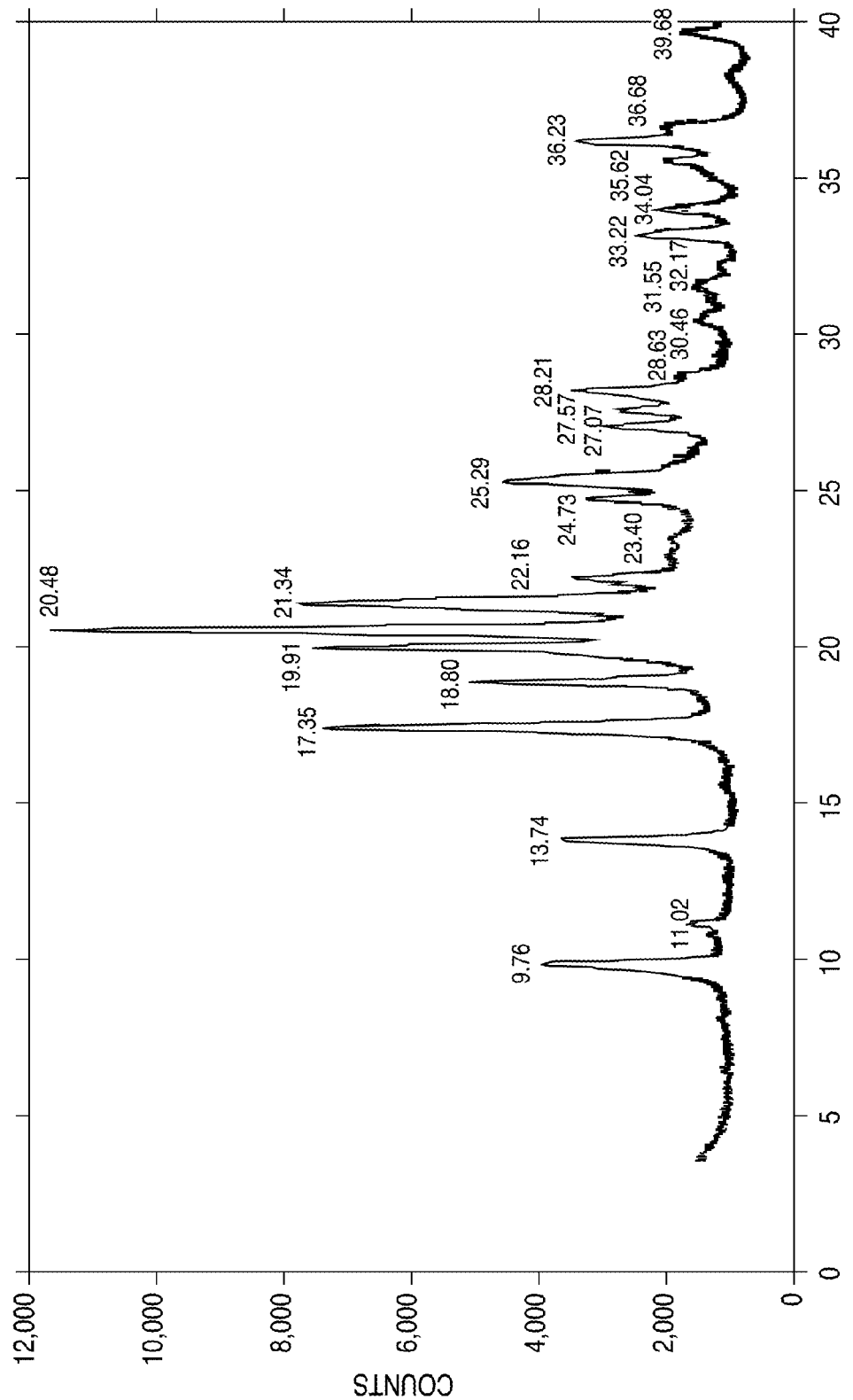
FIG. 5 provides an X-ray Powder Diffractogram (XRPD) of Batch 1, a solid dispersion of bendamustine hydrochloride with mannitol, substantially free of degradants.
Figure 6:
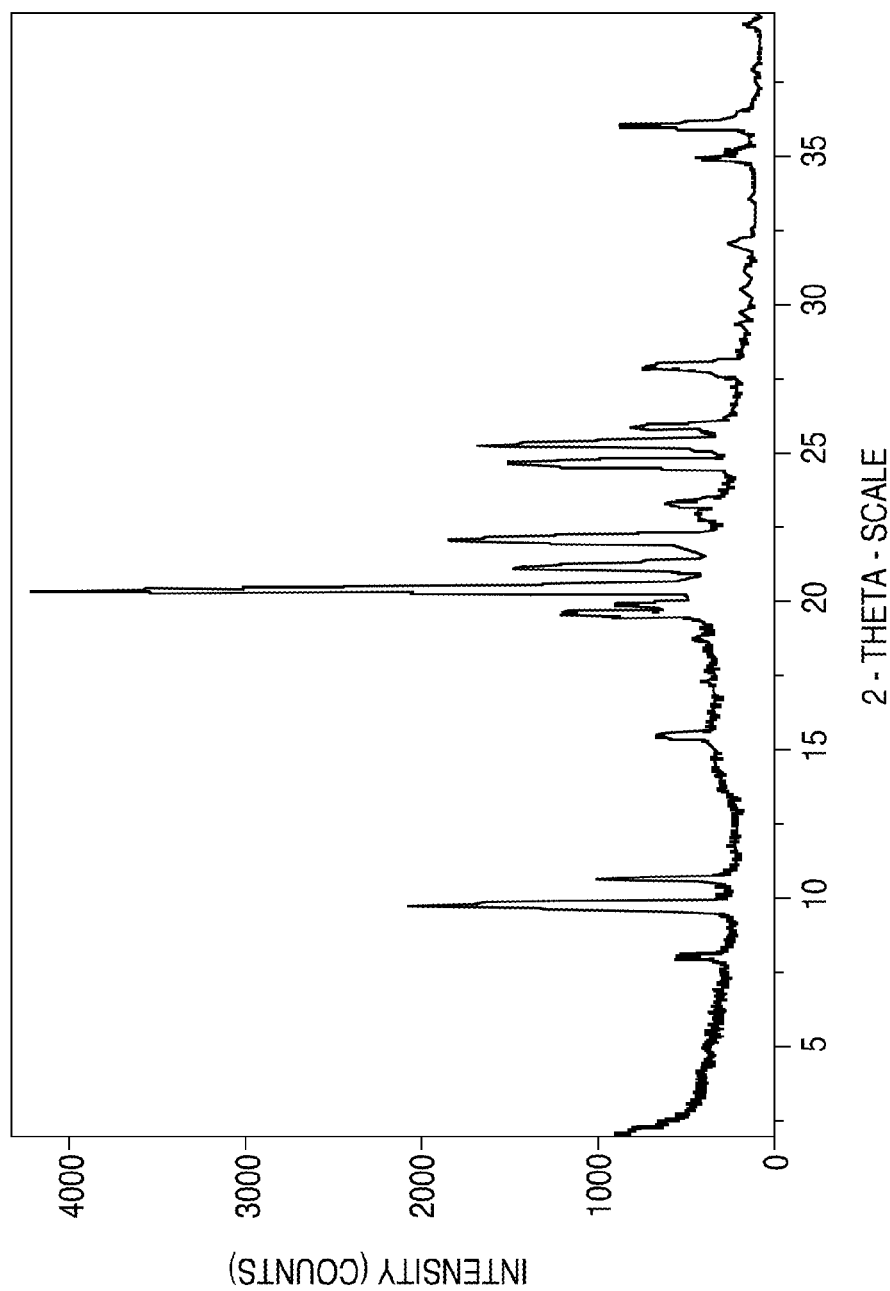
FIG. 6 provides an X-ray Powder Diffractogram (XRPD) of a lyophilized cake containing bendamustine hydrochloride and mannitol as reported in U.S. Pat. No. 8,445,524.

X-ray Powder Diffractograms of three such solid dispersions, prepared in accordance with the spray drying procedures described herein and comprising bendamustine hydrochloride-mannitol, bendamustine hydrochloride-polyvinylpyrrolidone and bendamustine hydrochloride-hydroxypropylmethylcellulose acetate succinate are shown respectively in FIGS. 5, 7 and 9.

Other embodiments provide solid dispersions of bendamustine hydrochloride having an X-ray powder diffraction pattern substantially as depicted in FIG. 5.

Other embodiments provide solid dispersions of bendamustine hydrochloride having an X-ray powder diffraction peak profile substantially as shown in Tab. 4.

Other embodiments provide solid dispersions of bendamustine hydrochloride having an X-ray powder diffraction pattern substantially as depicted in FIG. 7.

Other embodiments provide solid dispersions of bendamustine hydrochloride having an X-ray powder diffraction pattern substantially as depicted in FIG. 9.

Other embodiments provide a spray dried composition comprising a bendamustine hydrochloride crystalline form other than the monohydrate form.

Other embodiments provide a spray dried composition comprising a bendamustine hydrochloride crystalline form other than the form that exhibits peaks on an XRPD diffractogram at angles 8.3, 14, 16.8, 18.5±0.2 degrees 2θ (Form 1) or peaks at 7.9, 10.6, 15.5, 19.7±0.2 degrees 2θ (Form 3).

Also provided are spray dried compositions described herein further comprising amorphous bendamustine hydrochloride. A preferred embodiment provided herein includes a spray dried composition as described herein, comprising amorphous bendamustine hydrochloride, crystalline bendamustine hydrochloride, and a pharmaceutically acceptable excipient. An even more preferred embodiment provided herein includes a spray dried composition as described herein, comprising amorphous bendamustine hydrochloride and a pharmaceutically acceptable excipient.

Methods of Preparation

In another aspect, provided herein are methods of preparing the solid dispersions, pharmaceutical compositions, and pharmaceutical dosage forms. The solid dispersions can be prepared according to standard techniques. In particular embodiments, the solid dispersions are prepared by spray-dried solid dispersion, fluidized bed spray-dried solid dispersion, or spray granulation solid dispersion techniques known to those of skill or described herein.

Preferred methods of preparing solid dispersions of bendamustine hydrochloride comprise combining bendamustine hydrochloride with at least one solvent to form a solution and then drying the solution through spray drying or equivalent. In some embodiments, spray drying is conducted a continuous mode of operation in combination with a continuous pre-drying step as disclosed in co-pending U.S. patent application Ser. No. 14/466,765 filed on Aug. 22, 2014 the entirety of which is incorporated herein by reference.

A pharmaceutically acceptable excipient, suitable for spray drying, can be dissolved in the aqueous phase. Examples of useful excipients include, without limitation, sodium or potassium phosphate, sodium chloride, citric acid, tartaric acid, gelatin, glycine, and carbohydrates such as lactose, sucrose, maltose, glycerin, dextrose, dextran, trehalose and hetastarch. Mannitol is a preferred excipient. Other excipients that may be used if desired include antioxidants, such as, without limitation, ascorbic acid, acetylcysteine, cysteine, sodium hydrogen sulfite, butyl-hydroxyanisole, butyl-hydroxytoluene or alpha-tocopherol acetate, or chelators.

A pharmaceutically acceptable excipient, suitable for spray drying, can also be dissolved in the non-aqueous phase containing bendamustine. Examples of useful excipients include, without limitation polyvinylpyrrolidone, polyethylene glycols, polymethacrylates, hydroxypropylmethylcellulose, hydroxypropylmethylcellulose acetate succinate, ethylcellulose, hydroxypropylcellulose, cyclodextrins, or a mixture thereof. More preferred pharmaceutical excipients are polyvinylpyrrolidone, hydroxypropylmethylcellulose acetate succinate.

A typical formulation and spray drying run useful in accordance with the present description is provided below. Spray drying can be carried out using standard equipment as used for spray drying. The drying run may be varied depending upon the equipment and facilities used for production.

Figure 10:
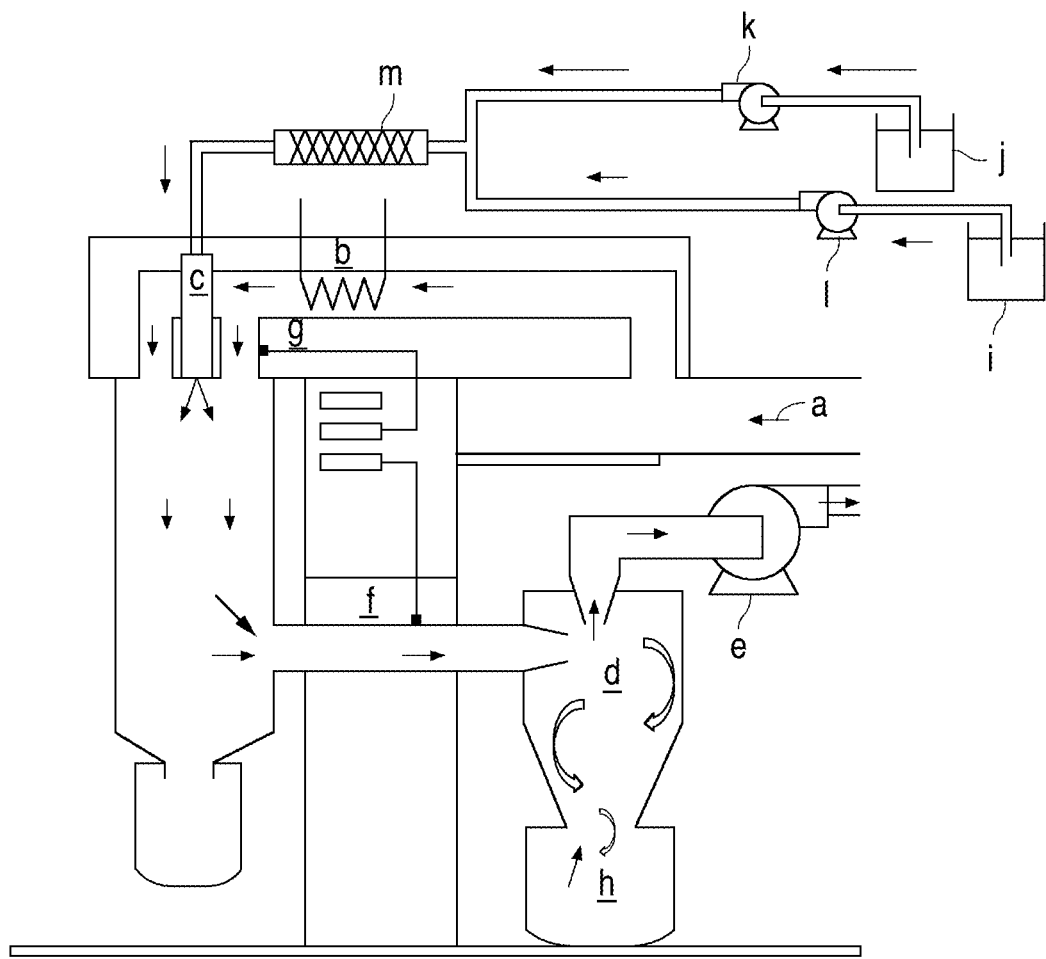
FIG. 10 provides a drawing of the spray drying system that may be used to obtain the solid dispersions of bendamustine hydrochloride when water miscible organic solvents are to be used. In the figure, the following components and features are indicated:
- a) Process gas in
- b) Process gas heat exchanger;
- c) Flow stabilized inlet to the drying chamber;
- d) Cyclone. Product is separated from process gas;
- e) Air blower;
- f) Temperature indicator of incoming process gas;
- g) Temperature indicator of outgoing process gas;
- h) Collection container;
- i) Non-Aqueous bendamustine pre-drying solution;
- j) Aqueous excipient pre-drying solution;
- k) Pump;
- l) Pump; and
- m) In-line static mixer.
Figure 11:
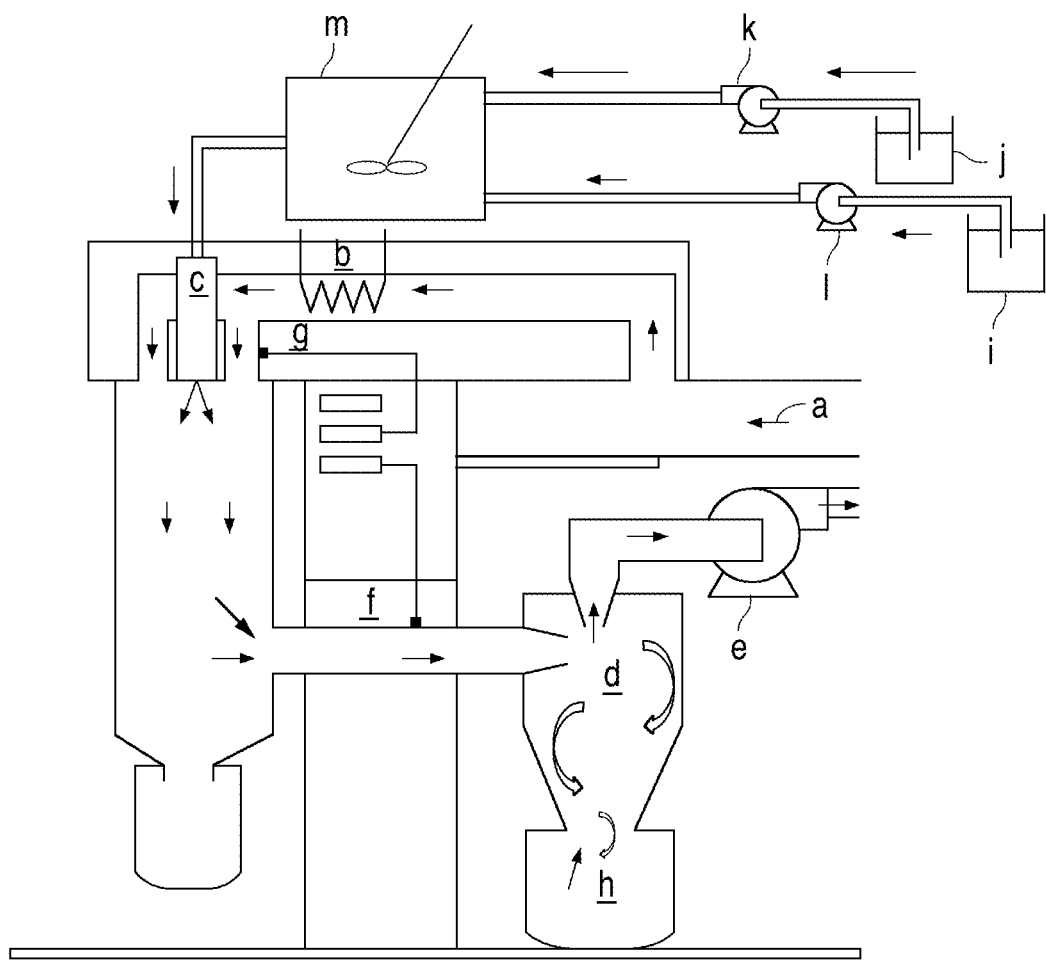
FIG. 11 provides a drawing of the spray drying system that may be used to obtain the solid dispersions of bendamustine hydrochloride when water immiscible or partially miscible organic solvents are to be used. In the figure, the following components and features are indicated:
- a) Process gas in
- b) Process gas heat exchanger;
- c) Flow stabilized inlet to the drying chamber (details in Drawing 2);
- d) Cyclone. Product is separated from process gas;
- e) Air blower;
- f) Temperature indicator of incoming process gas;
- g) Temperature indicator of outgoing process gas;
- h) Collection container;
- i) Non-Aqueous bendamustine pre-drying solution;
- j) Aqueous excipient pre-drying solution;
- k) Pump;
- l) Pump; and
- m) High shear mixer—Continuous homogenizer.

In accordance with a typical embodiment provided herein, a non-aqueous pre-drying solution, emulsion or dispersion containing bendamustine is first formulated in a pharmaceutically acceptable compounding vessel by means of an organic solvent that is either water miscible, water immiscible or partially water miscible. An aqueous pre-drying solution, emulsion or dispersion containing an acceptable excipient is also formulated in a separate pharmaceutically acceptable compounding vessel. Both solutions are then aseptically filtered, mixed by means of a continuous device that combines both streams and then continuously fed into the spray drier. The continuous device that combines both streams is an in-line mixer (also known in the art as static mixer) (FIG. 10), a continuous high shear mixer, a continuous emulsifier (FIG. 11), a continuous homogenizer, a continuous disperser or a combination thereof. The in-line mixer is preferred in case the solvent used in the non-aqueous phase is water miscible. The continuous emulsifier and continuous high shear mixer is preferred in case the solvent is water immiscible. The continuous emulsifier and continuous high shear mixer is also preferred in case the solvent is partially water miscible and the concentration of partially miscible solvent is above the saturation point with water. In this case, two distinct phases are formed, a water rich phase and a solvent rich phase. The use of a continuous emulsifier will facilitate the uniform and fine dispersion of the solvent rich droplets within the water rich phase. The desired outcome is the establishment of dry particles with distinct concentration profiles of API and excipient across the surface and the body of the particle that optimize the reconstitution and flowability characteristics of the dry particle while maintaining dose uniformity per USP (905). In an embodiment provided herein, the aqueous and non-aqueous solutions are mixed in a two-liquid-phase nozzle of the spray drier as presented in U.S. patent application Ser. No. 14/466,765 filed on Aug. 22, 2014 which is entirely incorporated herein. Using spray drying techniques described herein the solution is spray-dried until a moisture content of about 0.01 to about 8.0 percent is achieved. Even lower moisture content could be achieved by secondary drying as is known in the art. In case a highly water miscible solvent and an in-line mixer are used, the resulting dry powder particles will have higher concentration uniformity across their surface and body. In case a water immiscible solvent and a continuous emulsifier are used, the resulting dry powder particles will have distinct areas of high bendamustine/low excipient and low bendamustine/high excipient concentrations across their surface and body. The resulting dry-powder is uniform per USP (905) and stable for about six months to greater than about 2 years, preferably greater than about 3 years at about 5° C. to about 25° C. and can be readily reconstituted with Sterile Water for Injection, or other suitable carrier, to provide liquid formulations of bendamustine, suitable for internal administration e.g., by parenteral injection. For intravenous administration, the reconstituted liquid formulation, i.e. the pharmaceutical composition, is preferably a solution.

In accordance with another embodiment provided herein, an aqueous pre-drying solution will not be utilized. The non-aqueous pre-drying solution, emulsion or dispersion containing bendamustine is first formulated in a pharmaceutically acceptable compounding vessel. The non-aqueous pre-drying solution, emulsion or dispersion may contain one or more acceptable excipients that can be dissolved in the non-aqueous solution in sufficient quantities. Preferred excipients include, for example, polyvinylpyrrolidone, polyethylene glycols, polypropyleneglycols, polymethacrylates, hydroxypropylmethylcellulose, hydroxypropylmethylcellulose acetate succinate, ethylcellulose, hydroxypropylcellulose cyclodextrins, or a mixture thereof. More preferred pharmaceutical excipients are polyvinylpyrrolidone, hydroxypropylmethylcellulose acetate succinate. The solution is then aseptically filtered and continuously fed into the spray drier. Using spray drying techniques described herein the solution is spray-dried until a moisture content of about 0.01 to about 8.0 percent is achieved. Even lower moisture contents could be achieved by secondary drying as is known in the art. The resulting dry-powder is uniform per USP (905) and stable for about six months to greater than about 2 years, preferably greater than about 3 years at about 5° C. to about 25° C. and can be readily reconstituted with Sterile Water for Injection, or other suitable carrier, to provide liquid formulations of bendamustine, suitable for internal administration e.g., by parenteral injection. For intravenous administration, the reconstituted liquid formulation, i.e., the pharmaceutical composition is preferably a solution. In another embodiment, the resulting dry-powder can be utilized to provide solid formulations of bendamustine, suitable for oral administration e.g. via tablets or capsules.

In accordance with another embodiment, an organic pre-drying solution will not be utilized. The aqueous pre-drying solution, emulsion or dispersion containing bendamustine is first formulated in a pharmaceutically acceptable compounding vessel. The pH and/or the chlorine ion concentration of the aqueous solution is adjusted so as to minimize hydrolysis degradant formation. The aqueous pre-drying solution, emulsion or dispersion may contain one or more acceptable excipients that can be dissolved in the aqueous solution in sufficient quantities. Preferred excipients include, for example sodium or potassium phosphate, sodium chloride, potassium chloride, calcium chloride, citric acid, tartaric acid, gelatin, glycine, and carbohydrates such as lactose, sucrose, maltose, glycerin, dextrose, dextran, trehalose, mannitol, hetastarch or combinations thereof. Mannitol is a preferred excipient. The solution is then aseptically filtered and continuously fed into the spray drier. Using spray drying techniques described herein the solution is spray-dried until a moisture content of about 0.01 to about 8.0 percent is achieved. Even lower moisture contents could be achieved by secondary drying as is known in the art. The resulting dry-powder is uniform per USP (905) and stable for about six months to greater than about 2 years, preferably greater than about 3 years at about 5° C. to about 25° C. and can be readily reconstituted with Sterile Water for Injection, or other suitable carrier, to provide liquid formulations of bendamustine, suitable for internal administration e.g., by parenteral injection. For intravenous administration, the reconstituted liquid formulation, i.e., the pharmaceutical composition is preferably a solution. In another embodiment, the resulting dry-powder can be utilized to provide solid formulations of bendamustine, suitable for oral administration e.g. via tablets or capsules.

The pre-drying aqueous solution, emulsion or dispersion normally is formulated in a pharmaceutically acceptable container by: 1) adding an excipient, such as mannitol with mixing to water at ambient temperature. The pre-drying non-aqueous solution, emulsion or dispersion is formulated in a pharmaceutically acceptable container by: 1) adding bendamustine HCl to the desired concentration with mixing, 2) cooling the solution to about 1° C. to about 30° C., preferably about 5° C. In another embodiment, the pre-drying non-aqueous solution or dispersion is formulated in a pharmaceutically acceptable container by: 1) adding one or more pharmaceutically suitable excipients like polyvinylpyrrolidone or hydroxypropylmethylcellulose acetate succinate to the desired concentration with mixing, 2) adding bendamustine HCl to the desired concentration with mixing, 2) cooling the solution to about 1° C. to about 30° C., preferably about 5° C. Although the preceding steps are shown in a certain order, it is understood that one skilled in the art can change the order of the steps and quantities as needed. Quantities can be prepared on a weight basis also.

The pre-drying non-aqueous and/or pre-drying aqueous solutions, emulsions or dispersions can be sterilized prior to spray drying. Sterilization is generally performed by aseptic filtration, e.g., through a 0.22 micron or less filter. Multiple sterilization filters can be used. Sterilization of the solution or dispersion can be achieved by other methods known in the art, e.g., radiation.

In this case, after sterilization, the solution(s) or dispersion(s) are ready for spray drying. In certain embodiments, the solutions will be filtered, combined, mixed and introduced into the spray drier in a continuous mode of operation. Usually the formulation is effectively and efficiently spray-dried in collection containers from which the product will be aseptically filled into the containers which the product is to be marketed in, such as, without limitation, a vial, as described herein and as known in the art.

Certain embodiments are directed towards containers containing the product in its marketed form, such as, without limitation, a vial containing a spray dried solid dispersion with an excipient/API weight ratio such that will allow to obtain regulatory approval and to optimize the performance of the drying operation while maintaining desirable dry powder physical, chemical, stability and flow characteristics (e.g. moisture level, powder morphology). Preferred embodiments are directed towards the use of mannitol/bendamustine weight ratio between 1 and 4. Even more preferred embodiments are directed towards a mannitol/bendamustine weight ratio between about 1.2 and about 2.0. Even more preferred embodiments are directed towards a mannitol/bendamustine weight ratio of about 1.7. Most preferred embodiments are directed towards a mannitol/bendamustine weight ratio of about 1.8 or about 1.2.

To assure sterility, the collection containers may undergo terminal sterilization before filling the product into the containers which the products is to be marketed in, such as, without limitation, a vial. Terminal sterilization can be achieved by methods known in the art, e.g. radiation.

A typical procedure for use in spray drying the pre-drying solutions, emulsions or dispersions is set forth below. However, a person skilled in the art would understand that modifications to the procedure or process may be made depending on such things as, but not limited to, the pre-drying solution, emulsion or dispersion and spray drying equipment.

Initially, the air flow of the spray drier is set to the desired operating rate. This rate depends on the desired quantity to be spray dried, the desired pressure drop across the spray drying system and the geometry and size of the spray drying apparatus and can be calculated by heat and energy balances as known in the art. The air will be heated by means of a heat exchanger. The heat duty of the heat exchanger is adjusted appropriately so as to obtain a targeted temperature at the outlet of the spray chamber. A preferred range for this temperature is between about 40° C. and about 120° C. An even more preferred temperature is between about 45° C. and about 90° C. An even more preferred temperature is between about 50° C. and about 80° C.

Next, the atomizer air flow rate into the spray nozzle of the spray drier is set to the desired operating value. This flow rate depends on the kind and geometry of the nozzle and the desired properties of the resulting dry-powder particles.

The feeding rate of the aqueous pre-drying solution, in case it is being utilized, is then ramped up to the desired flow rate. The feeding rate is adjusted appropriately so as to obtain a targeted temperature at the outlet of the spray chamber. A preferred range for this temperature is between about 40° C. and about 120° C. An even more preferred temperature is between about 45° C. and about 90° C. An even more preferred temperature is between about 50° C. and about 80° C.

The feeding rate of the non-aqueous pre-drying solution is then ramped up to the desired flow rate. In case both aqueous and non-aqueous solutions are utilized, the feeding rates are adjusted appropriately so as to obtain a desired ratio of bendamustine to mannitol and maintain a targeted temperature at the outlet of the spray chamber. A preferred weight ratio of mannitol to bendamustine is between about 1 to about 5. A more preferred weight ratio of mannitol to bendamustine is between about 1.1 to about 3. A more preferred weight ratio of mannitol to bendamustine is between about 1.2 to about 2. A more preferred weight ratio of mannitol to bendamustine is about 1.7. An even more preferred weight ratio of mannitol to bendamustine is about 1.8. An even more preferred weight ratio of mannitol to bendamustine is about 1.2. In case only a non-aqueous pre-drying solution or only an aqueous pre-drying solution is utilized, the desired ratio of bendamustine to the excipient is controlled by dissolving the appropriate amounts in the pre-drying solution. A preferred weight ratio of the excipient to bendamustine is then between about 1 to about 10. A preferred range for the outlet temperature is between about 40° C. and about 120° C. An even more preferred temperature is between about 45° C. and about 90° C. An even more preferred temperature is between about 50° C. and about 80° C.

Certain embodiments are directed towards a spray drying system where the temperature of the solid-gas separation system (e.g. cyclone) and/or the temperature of the collection container is maintained at a temperature close to or below the glass transition temperature of the excipient. In case of mannitol, the glass transition temperature is in the 10 to 18 degrees C. range. Thus a preferred system is a system that maintains the temperature of the cyclone and/or the collector between 10-18 degrees C. An even more preferred system is a system that maintains the temperature of the cyclone and/or the collector below 10 degrees C.

By optimizing the weight ratio of excipient to bendamustine (among other operating variables of the spray drying system), it is possible to obtain particles with an optimal trade-off of properties like particle diameter, residual moisture, residual organic solvent, various concentration profiles across the surface of and within the particle, particle hardness, particle porosity, etc.

Once the dried particles move out of the spray drying chamber, they will be separated by means of a solid-vapor separator. One such separator, without limitation, is a cyclone. The dried particles separated via the cyclone will be collected in a collector usually located at the bottom of the cyclone. A preferred range for the operating temperature of the cyclone and collector is ambient temperature. An even more preferred temperature range is below the glass transition temperature of the excipient used (e.g. mannitol) for the purpose of optimizing the physical characteristics of the dried particles collected in the collector.

While the system is in transient operating conditions, the resulting dry-powder is collected into appropriate containers at the outlet of the powder collection system. The dry powder collected during this phase is not the desired product. Once the system reaches steady-state, the collection containers are changed to appropriate pharmaceutical containers acting as collection containers. The dry powder that is now collected is the desired dry-powder bendamustine.

Once the desired quantity of dry-powder bendamustine is produced, the collection container is switched again and the system is ramped down in the reverse order. The dry powder collected during this phase is not the desired product.

After spray drying, the bendamustine dry-powder may be filled into containers, such as vials. Typically an aseptic powder filling machine will be used as known in the art. Typically, a vial will contain dry-powder including about 10-500 mg/vial, preferably about 100 mg/vial bendamustine and about 5 mg-2 g/vial, preferably about 170 mg/vial mannitol. In another embodiment a vial will contain dry-powder including about 25 mg/vial bendamustine and about 42.5 mg/vial mannitol. In more preferred embodiment a vial will contain a dry-powder including about 10-500 mg/vial, preferably about 100 mg/vial bendamustine and about 5 mg-2 g/vial, preferably about 120 mg/vial mannitol. In another preferred embodiment a vial will contain dry-powder including about 25 mg/vial bendamustine and about 30 mg/vial mannitol. Several representative samples can be removed for purposes of performing various physical, chemical, and microbiological tests to analyze the quality of the product.

The dry-powder bendamustine formulation is typically marketed in pharmaceutical dosage form. The pharmaceutical dosage form, although typically in the form of a vial, may be any suitable container, such as ampoules, syringes, co-vials, which are capable of maintaining a sterile environment. Such containers can be glass or plastic, provided that the material does not interact with the bendamustine formulation. The closure is typically a stopper, most typically a sterile rubber stopper, preferably a bromobutyl rubber stopper, which affords a hermetic seal.

The dry-powder formulations may be reconstituted with water, preferably Sterile Water for Injection, or other sterile fluid such as co-solvents, to provide an appropriate solution of bendamustine for administration, as through parenteral injection following further dilution into an appropriate intravenous admixture container, for example, normal saline.

Also within the scope provided is a method for preparing a spray dried composition comprising a crystalline form of bendamustine hydrochloride comprising the steps of combining bendamustine hydrochloride with at least one solvent to form a mixture; and spray drying the mixture. Preferably, methods include those wherein the solution further comprises an excipient. Preferably, the excipient is sodium phosphate, potassium phosphate, citric acid, tartaric acid, gelatin, glycine, mannitol, lactose, sucrose, maltose, glycerin, dextrose, dextran, trehalose, hetastarch, polyvinylpyrrolidone, polyethylene glycols, polymethacrylates, hydroxypropylmethylcellulose, hydroxypropylmethylcellulose acetate succinate, ethylcellulose, hydroxypropylcellulose cyclodextrins, or a mixture thereof. More preferred pharmaceutical excipients are polyvinylpyrrolidone, hydroxypropylmethylcellulose acetate succinate or a mixture thereof. Most preferably, the excipient is mannitol. Preferably, methods include those wherein the solvent is water, an organic solvent, or a mixture thereof. Preferably, the organic solvent is methanol, ethanol, n-propanol, iso-propanol, n-butanol, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, dimethyl acetamide, hexafluoroacetone, chlorobutanol, dimethyl sulfone, acetic acid, cyclohexane, n-methyl-2-pyrrolidone (NMP), dimethylformamide (DMF), perfluorohexane, perflenapent, hexafluorobenzene, perfluoromethylcyclohexane, Fluorinert, perfluorooctane, tertbutylmethylether, ethyl ether, ethyl formate, isopropyl acetate, toluene, methyl ethyl ketone, propyl acetate, or a mixture thereof. More preferably, the organic solvent is ethanol or perfluorohexane or perfluorooctane. Even more preferable, the organic solvent is n-propanol. Most preferably, the organic solvent is NMP or DMSO.

Methods of Use

Also provided herein are methods of treating diseases, such as, for example, chronic lymphocytic leukemia, Hodgkin's disease, non-Hodgkin's lymphoma, multiple myeloma, relapsed diffuse large B-cell lymphoma, or breast cancer, with a pharmaceutical composition provided herein. Preferably, the solid dispersions of bendamustine are used to treat chronic lymphocytic leukemia. Also preferred are methods of using the solid dispersions provided herein to treat indolent B-cell non-Hodgkin's lymphoma, in particular, indolent B-cell non-Hodgkin's lymphoma that has progressed during or within six months of treatment with, for example, rituximab or a rituximab-containing regimen.

In certain embodiments, the method comprises administering a therapeutically effective amount of a pharmaceutical composition provided herein directly to the patient (for example, when the pharmaceutical composition is a tablet or capsule). In other embodiments, the method comprises modifying a pharmaceutical composition provided herein before administration, such as by dissolving the composition in water or another solvent prior to administration. In these embodiments, the method comprises administering to the patient a therapeutically effective amount of a preparation prepared from a pharmaceutical composition provided herein. Preferably, the preparation is an injectable preparation. The injectable preparation may be administered subcutaneously, intracutaneously, intravenously, intramuscularly, intra-articularly, intrasynovially, intrasternally, intrathecally, intralesionally, intracranially or via infusion. Other conditions amenable to treatment utilizing the compositions and injectable preparations provided herein include small cell lung cancer, hyperproliferative disorders, and autoimmune diseases, such as rheumatoid arthritis, multiple sclerosis, and lupus. Some embodiments are directed to oral solid pharmaceutical dosage forms like for example tablets and capsules.

Preferably, the injectable dose administered is about 100 mg/m$^2$. Dosages of about 25 mg/m$^2$, 60 mg/m$^2$, 50 mg/m$^2$, 90 mg/m$^2$ and about 120 mg/m$^2$ administered intravenously, are also within the scope provided herein. Preferably, the dosage is administered intravenously over about 30 minutes or over about 60 minutes. Also preferred are methods of administration wherein the dosage is administered on days 1 and 2 of a 28-day cycle. In some embodiments, the dosage is administered in from 1 to 6 or from 1 to 8 cycles.

The injectable preparations described herein are in the form of a sterile injectable preparation, for example, as a sterile, injectable aqueous or oleaginous suspension or solution formulated according to techniques known in the art. Typically, the pharmaceutical compositions provided herein are substantially free of hydrolysis degradants and are formulated as spray dried powders which may be provided, for example, in vials containing 100 mg of drug per 80 mL or 50 mL or 20 mL vial. The injectable preparation may be prepared by reconstitution of a spray dried solid dispersion with Sterile Water for Injection and then further dilution with a pharmaceutically acceptable intravenous solution, such as, for example, 0.9% sodium Chloride, 5% dextrose in water (D5W), Lactated Ringers solution, or 0.45% Sodium Chloride/2.5% dextrose.

Preferably, the pharmaceutical compositions of bendamustine hydrochloride described herein are reconstituted into an injectable preparation, for example, with sterile water, in less than about 20 minutes. More preferably, reconstitution occurs in less than about 10 minutes, more preferably about 5 minutes. Even more preferably about 2 minutes. Even more preferably in about 1 minute. Most preferably in less than 1 minute.

Certain embodiments are directed towards a reconstitution process which includes reconstituting, preferably aseptically, 25 mg or 100 mg of bendamustine hydrochloride contained in a vial together with a sugar alcohol excipient like, for example, mannitol or a polymeric excipient like, for example, polyvinylpyrrolidone (PVP) or any of the other excipients provided herein. The reconstitution is performed with a suitable organic solvent in suitable amount like either 5 or 10 or 20 or 40 ml of ethanol or either 5 or 10, or 20 or 40 ml of DMSO. Other suitable solvents are the solvents provided herein. This yields a clear solution having a bendamustine HCL concentration of 1.0 or 2.5 or 5 or 10 or 15 mg/ml.

Figure 12:
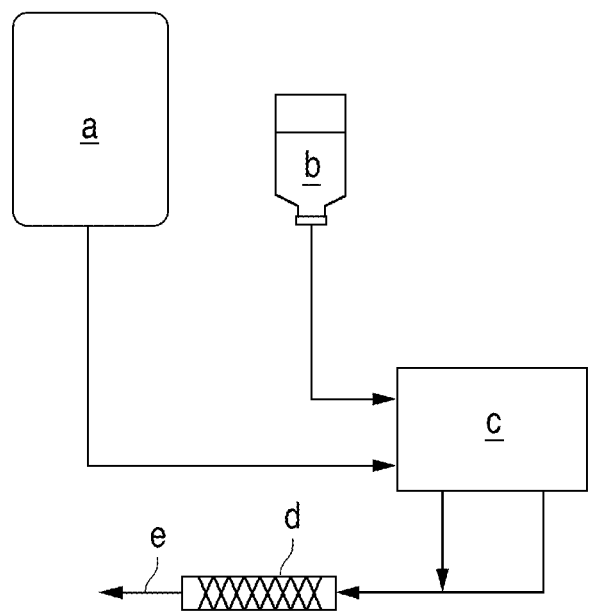
FIG. 12 provides a drawing of a continuous infusion system that minimizes the creation of hydrolysis degradants during infusion and is utilizing an infusion pump and an in-line (or static) mixer. The in-line mixer can be either integrated with or downstream of the pump. In the figure, the following components and features are indicated:
- a) Infusion bag containing diluent(s);
- b) Vial with Bendamustine in non-aqueous solution;
- c) Multichannel infusion pump;
- d) In-line mixer; and
- e) To patient.
Figure 13:
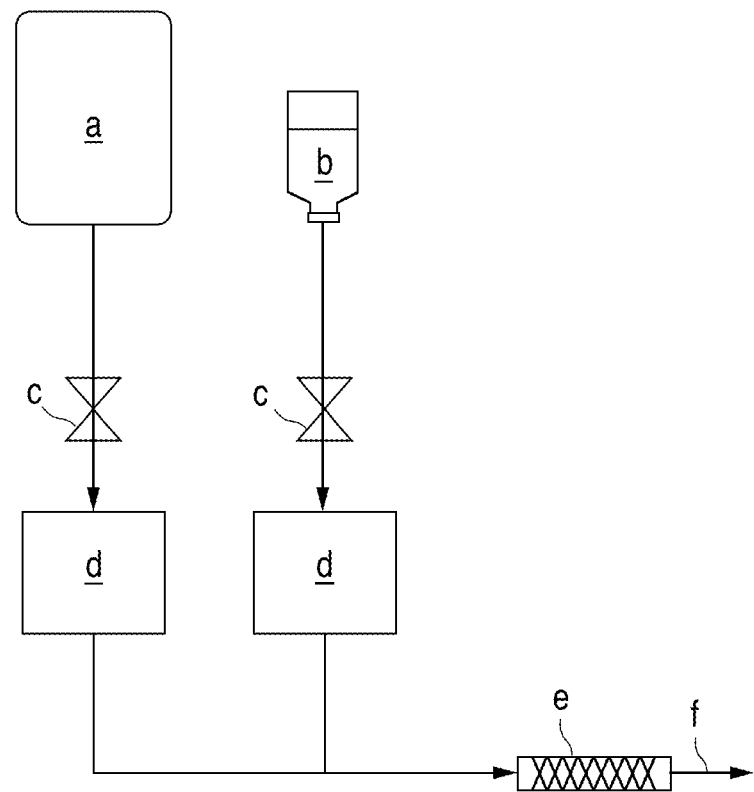
FIG. 13 provides a drawing of a continuous infusion system that minimizes the creating of hydrolysis degradants during infusion and its operation is driven by gravity. Desirable titration characteristics are being obtained through drip valves. In the figure, the following components and features are indicated:
- a) Infusion bag containing diluent(s)
- b) Vial with Bendamustine in non-aqueous solution
- c) Drip valves
- d) Drip chambers
- e) In-line mixer; and
- f) To patient.

If spray dried bendamustine hydrochloride is being reconstituted, the bendamustine hydrochloride should completely dissolve in less than 2 or 5 or 10 minutes. In case a continuous infusion system as shown in FIG. 12 or FIG. 13 is not utilized, the volume needed for the required dose concentration of 0.2, 0.3, 0.4, 0.6, 0.8, 1.0, 1.2 and 1.5 mg/mL post dilution based on the 1.0, 2.5, 5, 10, 15 mg/mL concentration pre dilution, can be aseptically withdrawn and transferred to a 100, 200, 250, 500 mL infusion bag of 0.9% Sodium Chloride (or other pharmaceutically acceptable intravenous solution as mentioned herein for injection.

In another aspect, provided are continuous infusion systems and methods for administering a solid dispersion, pharmaceutical composition, or dosage form provided herein. Examples of continuous infusion systems are provided FIG. 12 or FIG. 13. In the continuous infusion systems and methods, the nitrogen mustard compound is not added to an infusion bag. Instead, it is added directly and continuously in the infusion line that is delivering an infusion fluid to the bloodstream of a patient. Complete mixing of the two streams before entry to the patient's bloodstream can be accomplished by means of an in-line mixer (aka static mixer). Similar to the concept of continuously combining the pre-drying solutions described herein the contact time of bendamustine with water is minimized leading to the generation of very low amounts of hydrolysis degradants.

In certain embodiments, provided herein is a method for administering a nitrogen mustard compound. In the methods, an intravenous infusion solution is delivered in a continuous mode of operation to a patient in need thereof. A second solution comprising the nitrogen mustard compound is contacted with the intravenous infusion solution and is also delivered in a continuous mode of operation. The two solutions are mixed to provide a mixed solution. The mixed solution is administered to the patient to deliver a dose of the nitrogen mustard compound to the patient.

In certain embodiments, the nitrogen mustard compound can be any nitrogen mustard compound in any form described herein. In particular embodiments, the nitrogen mustard compound is bendamustine hydrochloride. In further embodiments, the nitrogen mustard compound is bendamustine hydrochloride with mannitol, as described herein.

The solution comprising the nitrogen mustard compound can be obtained by dissolving any solid form of the compound with a suitable solvent. In certain embodiments, the solid form is a solid dispersion as described herein. The solvent can be any solvent suitable for dissolving the compound and for administering to the patient. In particular embodiments, the solvent is DMSO. In other embodiments, the solvent is Water for Injection (WFI), n-propanol, ethanol, iso-propanol, n-butanol, ethyl acetate, dimethyl carbonate, acetonitrile, dichloromethane, methyl ethyl ketone, methyl isobutyl ketone, 1-pentanol, methyl acetate, carbon tetrachloride, dimethyl acetamide, hexafluoroacetone, chlorobutanol, dimethyl sulfone, acetic acid, cyclohexane, n-methyl-2-pyrrolidone (NMP), dimethylsulfoxide (DMSO), dimethylformamide (DMF) or mixtures thereof.

The nitrogen mustard compound can be provided at any concentration deemed suitable by the practitioner of skill. In particular embodiments, the nitrogen mustard compound is reconstituted, as referenced herein, at a concentration of about 1.0, 2.0, 2.5, 5.0, 7.5, 10.0, 15.0 mg/ml. Those of skill will recognize that this is the concentration of the nitrogen mustard compound prior to mixing with the intravenous infusion solution.

The intravenous infusion solution can be any intravenous infusion solution deemed suitable. In particular embodiments, the intravenous infusion solution can be 0.9% sodium chloride in water for injection. As will be apparent to those of skill, the intravenous infusion solution can be provided in any reservoir deemed suitable, such as an infusion bag.

The two solutions can be mixed by any technique deemed suitable. In certain embodiments, the solutions can be mixed by gravity or by agitation or by convection. In preferred embodiments, the solutions are mixed in a continuous mode of operation by an in-line mixer. The in-line mixer can be any in-line mixer deemed suitable to those of skill.

In certain embodiments, the intravenous solution is delivered to the mixer by a first tube. The intravenous solution can be delivered by any technique deemed suitable. In certain embodiments, the intravenous solution is delivered by gravity. In certain embodiments, the intravenous solution is delivered by drip, for example by one or more drip valves. In certain embodiments, the intravenous solution is delivered by one or more pumps.

In certain embodiments, the nitrogen mustard compound solution is delivered to the mixer by a second tube. The nitrogen mustard compound solution can be delivered by any technique deemed suitable. In certain embodiments, the nitrogen mustard compound solution is delivered by gravity. In certain embodiments, the nitrogen mustard compound solution is delivered by drip, for example by one or more drip valves. In certain embodiments, the nitrogen mustard compound solution is delivered by one or more pumps.

In particular embodiments, the flow rate of one or both solutions is controlled to control the concentrations of the components of the mixed solution. In certain embodiments, the flow rate for the intravenous infusion solution is from about 0.8 to about 50.0 ml/min. In particular embodiments, the flow rate of the intravenous infusion solution is about 16.67 ml/min. In certain embodiments, the flow rate of the nitrogen mustard compound solution is from about 0.08 to about 8.0 ml/min. In particular embodiments, the flow rate of the nitrogen mustard compound solution is about 0.334 ml/min. If the concentration of nitrogen mustard compound in the second solution is about 10 mg/ml, when the first flow rate is about 16.67 ml/min and the second flow rate is about 0.334 ml/min, the concentration of the nitrogen mustard compound in the mixed solution should be about 0.2 mg/ml and the combined infusion rate is about 17 ml/min. This means that 100 mg of bendamustine, when combined with 500 ml of an infusion solution, will be infused into the patient within a period of about 30 minutes. In other embodiments, the flow rate of the intravenous infusion solution is about 30.0 ml/min. The flow rate of the nitrogen mustard compound solution is about 1.8 ml/min. If the concentration of nitrogen mustard compound in the second solution is about 10 mg/ml, when the first flow rate is about 30.0 ml/min and the second flow rate is about 1.8 ml/min, the concentration of the nitrogen mustard compound in the mixed solution should be about 0.57 mg/ml and the combined infusion rate is about 31.8 ml/min. This means that 180 mg of bendamustine (corresponding to a dose of 100 mg/m2 for a normal adult), when combined with 300 ml of an infusion solution, will be infused into the patient within a period of about 10 minutes. As is known in the art, the increase in the infusion rate of bendamustine and/or the intravenous solution is limited by side effects to the patient like extravasation, local erythema, pain and swelling. It is also limited by the exceeding of the saturation point of dissolved bendamustine in the final infusion solution, which may result in precipitation and dose inconsistencies. Therefore, once the above two parameters are established for a particular infusion protocol, there is a large number of combinations of infusion variables like reconstitution concentration, reconstitution quantity, size of infusion liquid, speeds of infusion for reconstituted bendamustine and speed of infusion for intravenous solution, which are all within the scope of this invention.

In further embodiments, provided herein are apparatuses for continuous infusion of a nitrogen mustard compound. In certain embodiments, the continuous infusion apparatus comprises a first reservoir containing intravenous fluid, a first vessel configured to deliver the intravenous fluid to the in-line mixer, a second reservoir containing a nitrogen mustard compound solution, a second vessel configured to deliver the nitrogen mustard compound solution to the in-line mixer, and an in-line mixer configured to attain mixing of the two feed streams, and a third vessel configured to deliver the mixed solution to a delivery device capable of delivering the mixed solution to the bloodstream of the patient.

The delivery device can be any delivery device suitable for delivering an infusion solution to a patient. In certain embodiments, the delivery device is a catheter, an intravenous tube or vessel, or a needle.

The nitrogen mustard compound solution can be any such solution described herein. In particular embodiments, the nitrogen mustard compound solution is a reconstituted solid dispersion provided herein. In particular embodiments, the nitrogen mustard compound solution is reconstituted bendamustine hydrochloride, as described herein. In particular embodiments, the solution is substantially free of degradants such as nitrogen mustard compound degradants. In particular embodiments, the solution is substantially free of degradants such as nitrogen mustard compound hydrolysis degradants.

In the methods and apparatuses, those of skill will recognize that the nitrogen mustard compound solution mixes with the intravenous solution for a minimal amount of time prior to entering the bloodstream of the patient.

In the system shown in FIG. 12, the contents of an infusion bag containing 700 ml, 500 ml, 300 ml, 200 ml, or 100 ml of 0.9% Sodium Chloride (or other pharmaceutically acceptable infusion diluent) are continuously pumped, via means of a multichannel infusion pump, through an in-line mixer where they are mixed with the contents of reconstituted bendamustine which has been reconstituted as described herein. The reconstituted bendamustine is also continuously pumped, via means of an alternative channel of the same multichannel infusion pump, into the in-line mixer. By appropriately controlling the flow rates of the infusion pump feed channels, the appropriate concentration of the desired solution for infusion will be obtained. The desired concentration post dilution is about 0.2, 0.3, 0.4, 0.6, 0.8, 1.0, 1.5, 2.0, 3.0, 4.0 mg/ml bendamustine hydrochloride.

In the system shown in FIG. 13, the contents of an infusion bag containing 700 ml, 500 ml, 300 ml, 200 ml, or 100 ml of 0.9% Sodium Chloride (or other pharmaceutically acceptable intravenous solutions) are continuously dripped, via means of a drip control valve, into a drip chamber and, through an in-line mixer where they are mixed with the contents of the reconstituted bendamustine. The reconstituted bendamustine is also continuously dripped, via means of another drip control valve, into a separate drip chamber and then through the same in-line mixer. By appropriately controlling the flow rates through the drip pumps, the appropriate titration of the desired solution for infusion will be obtained. Flow can be sustained either through gravity or through applying pressure upstream. The desired concentration post dilution is 0.2, 0.3, 0.4, 0.6, 0.8, 1.0, 1.5, 2.0, 3.0, 4.0 mg/ml bendamustine hydrochloride.

Advantageously, continuous infusion can minimize the contact time of bendamustine with water and thus significantly reduce the creation of hydrolysis degradants. It is envisioned that the pharmaceutical compositions provided herein can be administered in combination with one or more anti-neoplastic agents where the antineoplastic agent is given prior to, concurrently with, or subsequent to the administration of the composition provided herein. Pharmaceutically acceptable anti-neoplastic agents are known in the art. Preferred anti-neoplastic agents are those disclosed in co-pending U.S. patent application Ser. No. 14/466,765 filed on Aug. 22, 2014 the entirety of which is incorporated herein by reference.

Also provided herein is the use of the continuous infusion systems, for instance as shown in FIG. 12 or FIG. 13, to continuously combine a pharmaceutically acceptable aqueous infusion diluent with a non-aqueous solution of a nitrogen mustard based antineoplastic agent so as to minimize the creation of hydrolysis degradants. Such antineoplastic agents include cyclophosphamide, bendamustine, bisulfan, chlorambucil, carmustin, melphalan, uramustine, ifosfamide, mechlorethamine, lumustine or combinations thereof. The non-aqueous solutions contain an organic solvent such as methanol, ethanol, n-propanol, iso-propanol, n-butanol, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide (DMSO), dimethyl acetamide, hexafluoroacetone, chlorobutanol, dimethyl sulfone, acetic acid, cyclohexane, n-methyl-2-pyrrolidone (NMP), dimethylformamide (DMF), tertbutylmethylether, ethyl ether, ethyl formate, isopropyl acetate, toluene, methyl ethyl ketone, propyl acetate or mixtures thereof.

Preferably, the pharmaceutical compositions of bendamustine hydrochloride described herein are reconstituted into an injectable preparation, for example, with sterile water or a non-aqueous solvent, that is a clear solution free of particulates. As a result, the pharmaceutical dose injected to the patient is uniform and consistent across administrations.

Certain embodiments provide a reconstitution process that includes reconstituting, preferably aseptically, 100 mg bendamustine hydrochloride with 20 mL Sterile Water for Injection. An alternative to this is to reconstitute 100 mg of bendamustine hydrochloride with 40 mL of Sterile Water for Injection. This yields a clear, colorless to pale yellow solution having a bendamustine HCl concentration of 5 mg/mL (or 2.5 mg/mL for the alternative reconstitution protocol). If spray dried bendamustine hydrochloride is being reconstituted, the bendamustine hydrochloride should completely dissolve in less than 2 minutes. The volume needed for the required dose (based on both the 5 mg/mL and the 2.5 mg/mL concentrations) can be aseptically withdrawn and transferred to a 500 mL infusion bag of 0.9% Sodium Chloride (or other pharmaceutically acceptable intravenous solution) for injection.

Preferably, if the continuous infusion method is not utilized, the reconstituted solution is transferred to the infusion bag within 30 minutes of reconstitution. After transfer, the contents of the infusion bag are thoroughly mixed. Administration by intravenous infusion is typically provided over a time period of from about 30 to about 60 minutes. In certain emobodiments infusion is provided over a time of 5, 10, 15, 20 minutes. It is envisioned that the pharmaceutical compositions provided herein can be administered in combination with one or more anti-neoplastic agents where the antineoplastic agent is given prior to, concurrently with, or subsequent to the administration of the composition provided herein. Pharmaceutically acceptable anti-neoplastic agents are known in the art. Preferred anti-neoplastic agents are those disclosed in co-pending U.S. patent application Ser. No. 14/466,765 filed on Aug. 22, 2014 the entirety of which is incorporated herein by reference.

Certain embodiments provided herein are directed to infusion protocols that call for transferring the reconstituted solution into an infusion bag with less than 500 mL volume of 0.9% Sodium Chloride (or other pharmaceutically acceptable intravenous solution) and administration by intravenous infusion over a time period less than 30 minutes. For example the use of 200 mL volume of 0.9% Sodium Chloride and 12 minute infusion time.

Therapeutically effective amounts of bendamustine can be readily determined by an attending diagnostician by use of conventional techniques. The effective dose can vary depending upon a number of factors, including type and extent of progression of the disease or disorder, overall health of a particular patient, biological efficacy of bendamustine, formulation of bendamustine, and route of administration of the forms of bendamustine. Bendamustine can also be administered at lower dosage levels with gradual increases until the desired effect is achieved.

Also within the scope provided herein are methods of treating chronic lymphocytic leukemia, Hodgkin's disease, non-Hodgkin's lymphoma, multiple myeloma or breast cancer comprising administering to a patient in need thereof a therapeutically effective amount of a preparation prepared from a composition as described herein.

EXAMPLES

The following Examples are provided to illustrate certain aspects of the present description and to aid those skilled in the art in practicing the description. These Examples are in no way to be considered to limit the scope of the description in any manner.

Materials: Bendamustine HCL, (Tianjin Pharmacn Medical Technology Co, Ltd, Batch #130801); Mannitol, Pearlitol 160C (Roquette, Lot#52305973); PVP, Plasdone K-17 (Ashland, Product Code 1172625, Lot#052305973); HPMCAS, Aquasolve HPMC-AS MF (Ashland, Product Code834121, Lot# ASHMA 1004F); Ethyl Alcohol, USP grade UN1170, (200 proof) (Koptec, PN V1001); n-propanol (Macron Fine Chemicals, Batch#0000040691); Methanol, (Omnisolv, MX0488-6).

Equipment: Agilent 1100 series equipped with a UV detector; Zorbax SB-C18, 4.6×250 mm, 5 um; Rigaku Smart-Lab X-ray diffraction system, TA Instruments Q2000 DSC system, TA Instruments Q50 TG system, Leica M80 stereo microscope with a PAXcam3 digital camera, Buchi B-191 spray drier, PANalytical X'Pert PRO MPD difractometer using an incident beam of Cu Kα radiation produced using a long, fine-focus source and a nickel filter. Leica DM LP microscope equipped with Spot Insight color camera. Unless noted, crossed polarizers with a first order red compensator were used.

Example 1

HPLC Procedures

Bendamustine and bendamustine degradation products were measured by high performance liquid chromatography according to Method 1 or Method 2, below.

| Method 1 | |
|---|---|
| Parameter | Value |
| Column | Zorbax SB-C18, 4.6 × 250 mm, 5 um with C18 4 × 3 mm Phenomenex Security Guard |
| Column Temperature | 30° C. |
| Detector wavelength | 230 nm |
| Mobile Phase A: | 0.1% TFA in water |
| Mobile Phase B: | 0.1% TFA in water:ACN (1:1) |
| Gradient: | 0 min, 20% B |
| | 1 min, 20% B |
| | 24 min, 90% B |
| | 30 min, 90% B |
| | 31 min, 20% B |
| Injection Volume: | 10 uL |
| Flow rate: | 1.0 mL/min |
| Run time: | 36 min |

Results:

The retention times for some Bendamustine impurities using Method 1 described above, are shown in Table 1.

TABLE 1

| Retention Time for Bendamustine and some of its impurities using HPLC method 1 | |
|---|---|
| Sample Name | Retention Time (min) |
| HP2 | 6.8 |
| HP1 | 12.8 |
| Bendamustine | 20.3 |
| Bendamustine Methlylester | 21.7 |
| Dimer | 23.3 |

HP2 is the compound resulting from further hydrolysis of HP1 seen in Formula V.

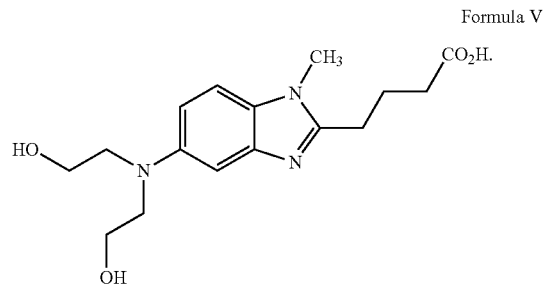 [SMILES: Cn1c(CCCC(=O)O)nc2cc(N(CCO)CCO)ccc21]

Formula V

Example 2

Bendamustine/Mannitol Based Compositions Free of Hydrolysis Degradants

Two batches (Batch 1 and Batch2) each one with a different pharmaceutical composition comprising solid dispersions in the form of dry powder and substantially free of hydrolysis degradants were produced. For each batch, two pre-drying intermediate compositions were formulated in separate containers. For Batch 1, the aqueous pre-drying composition was formulated consisting of 2380 mg of mannitol dissolved in 70 ml of water. The non-aqueous pre-drying composition was formulated by dissolving 1400 mg of bendamustine in 70 ml of n-propanol. For Batch 2, the aqueous pre-drying composition consisted of 1190 mg of mannitol dissolved in 70 ml of water. The non-aqueous pre-drying composition was formulated by dissolving 700 mg of bendamustine hydrochloride in 70 ml of ethanol. The ethanol/bendamustine solution could be cooled to minimize the extent of possible side reactions. Both feed pumps (see FIG. 10) were set in such a way that the ratio of excipient to API was 1.8 for Batch 1 and 1.9 for Batch 2. Tables 2 and 3 show the process parameters for Batch 1 and Batch 2.

The spray dried powder obtained was consisting of fine particles of white color. The batches were tested for residual moisture, residual solvent (via TGA) and concentration of degradants. (HP2 related compounds, HP1 related compounds, dimer, methylester and ethylester of bendamustine). The results can be seen on Table 4.

As seen on Table 5 which contains the XRPD peak data for Batch 1, the significant crystalline peaks in this solid dispersion can be attributed to mannitol polymorphs delta and alpha. No peaks that correspond to bendamustine form 1 or bendamustine form 3 were observed. (i.e. no peaks at 8.3, 14, 16.8, 18.5±0.2 degrees 2θ for Form 1 or peaks at 7.9, 10.6, 15.5, 19.7±0.2 degrees 2θ for Form 3).

Light microscopy was performed using a Leica DM LP microscope equipped with Spot Insight color camera. Unless noted, crossed polarizers with a first order red compensator were used. 5×, 10×, 20× and 40× objectives were used to view the sample. The sample was placed on a glass microscope slide, a 1½ cover glass was placed over the sample, and mineral oil was added to the edge of the cover glass to cover the sample by capillarity. Dry mount were used when referred to in the figures. Images were acquired at ambient temperature using Spot Advanced software (v.4.5.9). Micrometer bars were inserted onto the images as a reference for particle size.

TABLE 2

Process Parameters for Example 2

| | Feed rate (combined) (g/min) | Atomizer Pressure (psi) | Atomizer gas flow (g/sec) | ALR ratio | Temp Inlet (° C.) | Temp outlet (° C.) | Run Time (min) |
|---|---|---|---|---|---|---|---|
| Batch 1 | 2.27 | 50 | 0.57 | 15.0 | 115 | 85 | 55 |
| Batch 2 | 2.43 | 50 | 0.57 | 14.0 | 115 | 85 | 49 |

TABLE 3

Additional Process Parameters for Example 2

| | API (gr) | Excipient (gr) | Ratio Excipient/API | Solvent | Total Solids (gr) | Total Solids (% TS) |
|---|---|---|---|---|---|---|
| Batch 1 | 1.4 | 2.380 | 1.8 | Propanol | 3.78 | 3.0% |
| Batch 2 | 0.7 | 1.190 | 1.9 | Ethanol | 1.89 | 1.5% |

TABLE 4

Test Results for Example 2.

| | HP2 (% Area) | HP1 (% Area) | Bendamustine (% Area) | Dimer (% Area) | Moisture (% w/w) | Residual Solvent (% w/w) |
|---|---|---|---|---|---|---|
| Batch 1 | ND | ND | 100.0 | ND | 0.34 | ND |
| Batch 2 | ND | ND | 100.0 | ND | 0.32 | 0.07 |

TABLE 5

Observed XRPD peaks for batch 1

| °2θ | d space (Å) | Intensity (%) |
|---|---|---|
| 9.76 ± 0.20 | 9.055 ± 0.185 | 35 |
| 11.02 ± 0.20 | 8.022 ± 0.145 | 15 |
| 13.74 ± 0.20 | 6.440 ± 0.093 | 33 |
| 17.35 ± 0.20 | 5.107 ± 0.058 | 64 |
| 18.80 ± 0.20 | 4.716 ± 0.050 | 45 |
| 19.91 ± 0.20 | 4.456 ± 0.044 | 65 |
| 20.48 ± 0.20 | 4.333 ± 0.042 | 100 |
| 21.34 ± 0.20 | 4.160 ± 0.039 | 68 |
| 22.16 ± 0.20 | 4.008 ± 0.036 | 30 |
| 23.40 ± 0.20 | 3.799 ± 0.032 | 17 |
| 24.73 ± 0.20 | 3.597 ± 0.029 | 29 |
| 25.29 ± 0.20 | 3.519 ± 0.027 | 39 |
| 27.07 ± 0.20 | 3.291 ± 0.024 | 26 |
| 27.57 ± 0.20 | 3.233 ± 0.023 | 24 |
| 28.21 ± 0.20 | 3.161 ± 0.022 | 31 |
| 28.63 ± 0.20 | 3.116 ± 0.021 | 16 |
| 30.46 ± 0.20 | 2.932 ± 0.019 | 13 |
| 31.55 ± 0.20 | 2.833 ± 0.018 | 14 |
| 32.17 ± 0.20 | 2.780 ± 0.017 | 11 |
| 33.22 ± 0.20 | 2.695 ± 0.016 | 22 |
| 34.04 ± 0.20 | 2.632 ± 0.015 | 19 |

TABLE 5-continued

Observed XRPD peaks for batch 1

| °2θ | d space (Å) | Intensity (%) |
|---|---|---|
| 35.62 ± 0.20 | 2.518 ± 0.014 | 18 |
| 36.23 ± 0.20 | 2.477 ± 0.013 | 29 |
| 36.66 ± 0.20 | 2.449 ± 0.013 | 18 |
| 39.63 ± 0.20 | 2.272 ± 0.011 | 16 |

FIG. 3 shows particles from Batch 1 observed through Polarized Light Microscopy. We noted that the particles and particle aggregates exhibit birefringence, uniformity and diameters in the 20-200 micrometers. The nature of birefringence, combined with the XRPD data indicate that the solid dispersion constitutes primarily of amorphous bendamustine embedded in a crystalline mannitol matrix.

As seen on Table 6 which shows the XRPD peak data for Batch 2, the significant crystalline peaks in this solid dispersion can be attributed to mannitol polymorphs delta and alpha. Some peaks that may correspond to bendamustine form 3 were observed (i.e. peaks at 7.9, 10.6, 15.5, 19.7±0.2 degrees 2θ). Thus, we surprisingly found that the modifications in experimental conditions between Batch 2 and Batch 1 were sufficient to enable the production of solid dispersions that contain bendamustine Form 3 in addition to mannitol and other forms of bendamustine.

Based on the above we unexpectedly found that under a certain set of process parameters, it is possible to produce uniform solid dispersions, in dry powder form, substantially free of hydrolysis degradants and comprising amorphous bendamustine and crystalline mannitol which are substantially free of crystalline forms of bendamustine. Certain embodiments described herein comprise trace amounts of crystalline bendamustine, in addition to amorphous bendamustine, which, in any case, will be substantially free of the bendamustine crystalline polymorph Form 1 or Form 3.

TABLE 6

Observed XRPD peaks for batch 2

| °2θ | d space (Å) | Intensity (%) |
|---|---|---|
| 8.06 ± 0.20 | 10.963 ± 0.272 | 11 |
| 9.81 ± 0.20 | 9.013 ± 0.183 | 38 |
| 10.63 ± 0.20 | 8.314 ± 0.156 | 12 |
| 11.04 ± 0.20 | 8.005 ± 0.145 | 13 |
| 13.78 ± 0.20 | 6.422 ± 0.093 | 26 |
| 15.55 ± 0.20 | 5.694 ± 0.073 | 10 |
| 17.39 ± 0.20 | 5.094 ± 0.058 | 54 |
| 18.86 ± 0.20 | 4.701 ± 0.049 | 35 |
| 19.97 ± 0.20 | 4.442 ± 0.044 | 61 |
| 20.53 ± 0.20 | 4.323 ± 0.042 | 100 |
| 21.38 ± 0.20 | 4.153 ± 0.038 | 65 |
| 22.18 ± 0.20 | 4.005 ± 0.036 | 34 |
| 23.40 ± 0.20 | 3.799 ± 0.032 | 20 |
| 24.78 ± 0.20 | 3.590 ± 0.029 | 31 |
| 25.37 ± 0.20 | 3.507 ± 0.027 | 44 |

TABLE 6-continued

Observed XRPD peaks for batch 2

| °2θ | d space (Å) | Intensity (%) |
|---|---|---|
| 27.13 ± 0.20 | 3.284 ± 0.024 | 24 |
| 27.64 ± 0.20 | 3.225 ± 0.023 | 23 |
| 28.22 ± 0.20 | 3.160 ± 0.022 | 27 |
| 30.50 ± 0.20 | 2.928 ± 0.019 | 13 |
| 30.68 ± 0.20 | 2.911 ± 0.019 | 13 |
| 31.23 ± 0.20 | 2.862 ± 0.018 | 12 |
| 31.61 ± 0.20 | 2.828 ± 0.017 | 14 |
| 32.24 ± 0.20 | 2.774 ± 0.017 | 11 |
| 33.26 ± 0.20 | 2.692 ± 0.016 | 20 |
| 34.09 ± 0.20 | 2.628 ± 0.015 | 18 |
| 35.67 ± 0.20 | 2.515 ± 0.014 | 18 |
| 36.27 ± 0.20 | 2.475 ± 0.013 | 33 |
| 36.68 ± 0.20 | 2.448 ± 0.013 | 19 |
| 39.67 ± 0.20 | 2.270 ± 0.011 | 15 |

The solid dispersions produced in Batch 1 and Batch 2, exhibit distribution uniformity between crystalline mannitol (that exhibits birefringence) and amorphous bendamustine (that doesn't exhibit birefringence) as can be seen in FIG. 3 and FIG. 4. This uniformity has also been verified by collecting and analyzing multiple samples from within a batch as well as through DSC.

FIG. 5 shows the XRPD diffractogram of Batch 1. Comparing this with the XRPD diffractogram of the lyophilized composition reported in U.S. Pat. No. 8,445,524 and shown in FIG. 6, we can see that not only the solid dispersion of batch 1 doesn't exhibit the prominent peaks at 7.9, 10.6, 15.5 and 19.7±0.2 degrees 2θ that are associated with bendamustine form 3, but we also observe that the mannitol polymorphs contained in the solid mixtures are different. (for example the peak at angle 13.74±0.2 degrees 2θ associated with mannitol polymorph alpha is not present in FIG. 6). This confirms that the compositions characterized by the two diffractograms are unique and separate in addition to exhibiting distinct physical and chemical properties.

Example 3

Amorphous Solid Dispersions

Two batches (Batch 3 and Batch4) each one with a different pharmaceutical composition comprising solid dispersions in the form of dry powder and free of hydrolysis degradants were produced. For each batch, one pre-drying intermediate composition was formulated in an acceptable container. This pre-drying intermediate composition comprised of an organic solvent, bendamustine hydrochloride and an excipient that is dissolvable in the organic solvent. No aqueous pre-drying solution was used. For Batch 3 was obtained by dissolving 600 mg of Bendamustine HCL and 3000 mg of Plasdone K-17 (Polyvinylpyrrolidone, PVP) in 120 ml of pure ethanol. The ratio of PVP to Bendamustine is 5:1. Thus, the Total Solids ratio for this batch was 3.0%. Batch 4 was obtained by dissolving 300 mg of Bendamustine HCL and 900 mg of HPMC-AS in 40 ml of pure methanol. The ratio of HPMC-AS to Bendamustine was 3:1. The Total Solids ratio for batch 4 was 3.8%.

TABLE 7

Process Parameters for Example 3

| | Feed rate (g/min) | Atomizer Pressure (psi) | Atomizer gas flow (g/sec) | ALR ratio | Temp Inlet (° C.) | Temp outlet (° C.) | Run Time (min) |
|---|---|---|---|---|---|---|---|
| Batch 3 | 2.09 | 50 | 0.57 | 16.3 | 81 | 63 | 45.7 |
| Batch 4 | 2.05 | 40 | 0.49 | 14.3 | 80 | 63 | 15.25 |

The spray dried powder obtained was consisting of fine particles of white color. The batches were tested for residual moisture, residual solvent (via TGA) and concentration of degradants. The results can be seen on Table 8.

Solid phase characterization tests were conducted on Batch 3 and 4. XRPD diffractograms can be seen in FIGS. 7 and 9 for Batch 3 and 4 respectively. From these diffractograms it was surprisingly found that although Bendamustine HCL has a tendency to crystallize, both solid dispersions with PVP and HPMC-AS were amorphous and substantially free of crystalline forms.

TABLE 8

Test Results for Example 3

| | HP2 (% Area) | HP1 (% Area) | Bendamustine (% Area) | Dimer (% Area) | Moisture (% w/w) | Residual Solvent (% w/w) |
|---|---|---|---|---|---|---|
| Batch 3 | ND | ND | 100.0 | ND | NA (*) | 0.54 (*) |
| Batch 4 | ND | ND | 100.0 | ND | 1.105 | 0.655% |

Notes:
(*) Moisture not measured. 0.54 is for both moisture and residual solvent.

Figure 8:
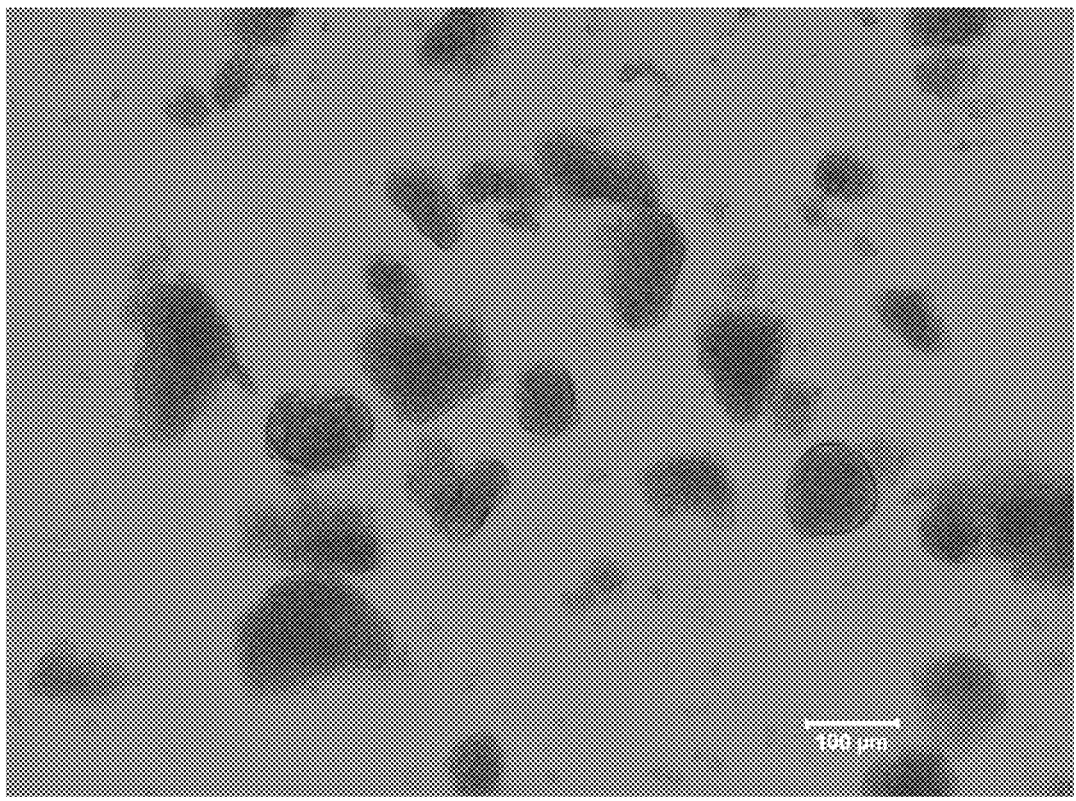
FIG. 8 provides a Polarized Light Microscopy image of particles from Batch 3, a solid dispersion of bendamustine hydrochloride with PVP, substantially free of degradants.

FIG. 8 shows a Polarized Light Microscopy picture for Batch 3. The lack of any birefringence confirms that the solid dispersion is in the form of dry powder particles comprising amorphous bendamustine in an amorphous PVP matrix.

Example 4

Continuous Infusion Process

A vial containing 100 mg of bendamustine and 500 mg of polyvinylpyrrolidone (PVP) is reconstituted by adding 39.6 ml of ethanol. By shaking and providing 10 minutes to allow complete dissolution, the non-aqueous solution is ready for infusion. The reconstituted solution is clear and free of particulates. The volume of the resulting solution is about 40 ml. The bendamustine concentration in the resulting solution is about 2.5 mg/ml. The vial with the reconstituted bendamustine is attached to the continuous infusion system shown in FIG. 12.

An infusion bag containing 500 ml of 0.9% sodium chloride aqueous solution for injection is attached to the continuous infusion system shown in FIG. 12. The infusion bag and the reconstituted vial are connected via pharmaceutically acceptable tubing to the multichannel infusion pump. The infusion pump has a small-volume infusion capability allowing the accurate control of flow rates at very small volumetric flow rates.

To obtain the desired infusion time of about 30 minutes, the flow rate for the channel dedicated to the aqueous sodium chloride solution is set to about 16.67 ml/min. The flow rate for the non-aqueous bendamustine solution is set to about 1.334 ml/min. Considering a bendamustine concentration of 2.5 mg/ml in the reconstituted vial, the mass flow rate of the non-aqueous bendamustine solution corresponds to about 3.334 mg/min of bendamustine.

Both aqueous 0.9% sodium chloride and non-aqueous ethanol/bendamustine solutions are continuously mixed through the in-line mixer as shown in FIG. 12. By appropriately providing enough residence time, turbulence and design features as is well known in the art of designing in-line mixers, both inflows are completely mixed and the solution at the outlet of the mixer is uniform. The bendamustine concentration in the solution infused into the patient is about 0.2 mg/ml.

The inner tube volume of the tubing between the outlet of the in-line mixer and the entry point to the patient is 0.1 ml and the in-line mixer volume is 0.5 ml. This means, for a combined flow rate of about 18 ml/min, that the time duration in which bendamustine is in direct contact with an aqueous solution is about 0.033 minutes or about 2 seconds. Considering this short duration time, in combination with the kinetics of the bendamustine hydrolysis reaction which has reaction half times measured in hours rather than seconds, one concludes that the continuous infusion system delivers to the patient a bendamustine solution substantially free of hydrolysis degradants.

Example 5

Continuous Infusion Process for a Mannitol/Bendamustine Formulation

A vial containing 100 mg of bendamustine and 120 mg of mannitol is reconstituted by adding 10 ml of DMSO. Alternatively, instead of DMSO, NMP, DMA, DMI, PEG, PG or glycerin could be used. The solubility of mannitol in DMSO is about the same as in water (~36 mg/ml) which means that the resulting solution is significantly removed from the saturation and precipitation point (i.e. at about 30% of saturation point). By shaking and providing 10 minutes to allow complete dissolution, the non-aqueous solution is ready for infusion. The reconstituted solution is clear and free of particulates. The volume of the resulting solution is about 10 ml. The bendamustine concentration in the resulting solution is about 10.0 mg/ml. The vial with the reconstituted bendamustine is attached to the continuous infusion system shown in FIG. 12.

An infusion bag containing 300 ml of 0.9% sodium chloride aqueous solution for injection is attached to the continuous infusion system shown in FIG. 12. The infusion bag and the reconstituted vial are connected via pharmaceutically acceptable tubing to the multichannel infusion pump. The infusion pump has a small-volume infusion capability allowing the accurate control of flow rates at very small volumetric flow rates.

To obtain a desired infusion time of about 10 minutes, the flow rate for the channel dedicated to the aqueous sodium chloride solution is set to about 30 ml/min. The flow rate for the non-aqueous bendamustine solution is set to about 1.0 ml/min. Considering a bendamustine concentration of 10.0 mg/ml in the reconstituted vial, the mass flow rate of the non-aqueous bendamustine solution corresponds to about 10.0 mg/min of bendamustine.

Both aqueous 0.9% sodium chloride and non-aqueous DMSO/bendamustine solutions are continuously mixed through the in-line mixer as shown in FIG. 12. By appropriately providing enough residence time, turbulence and design features as is well known in the art of designing in-line mixers, both inflows are completely mixed and the solution at the outlet of the mixer is uniform. The bendamustine concentration in the solution infused into the patient is about 0.32 mg/ml.

The inner tube volume of the tubing between the outlet of the in-line mixer and the entry point to the patient is about 0.1 ml and the in-line mixer volume is about 0.5 ml. This means that for a combined flow rate of 31 ml/min the time duration in which bendamustine is in direct contact with an aqueous solution is about 0.0193 minutes or 1.16 seconds. Considering this short duration time, in combination with the kinetics of the bendamustine hydrolysis reaction which has reaction half times measured in hours rather than seconds, one concludes that the continuous infusion system delivers to the patient a bendamustine solution substantially free of hydrolysis degradants.

All patents, patent applications, and publications mentioned in the specification are indicative of the levels of those of ordinary skill in the art to which the description pertains. All patents, patent applications, and publications are herein incorporated by reference to the same extent as if each individual publication was specifically and individually indicated to be incorporated by reference.

The description illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present description has been specifically disclosed by preferred embodiments and optional features, modification and variation of the concepts herein disclosed may be resorted to by those skilled in the art, and that such modifications and variations are considered to be within the scope of this description as defined by the appended claims.

What is claimed is:

1. A method for administering a dose of a nitrogen mustard compound to a patient comprising the steps of
   a. contacting a stream of an intravenous infusion solution continuously flowing at a controlled rate with a stream of a second solution continuously flowing at a controlled rate and comprising the nitrogen mustard compound and either 1) polyvinylpyrrolidone and ethanol, or 2) mannitol and a solvent selected from the group consisting of dimethylsulfoxide, n-methyl-2-pyrrolidone, dimethylacetamide, polyethylene glycol, propylene glycol, glycerin, and mixtures thereof;
   b. mixing the solutions to provide a uniform and continuously flowing stream of a mixed solution which provides a pharmaceutical dose of 0.2 to 4.0 mg/ml of the nitrogen mustard compound; and
   c. administering the mixed solution to the patient, thereby administering the pharmaceutical dose of the nitrogen mustard compound to the patient, wherein the residence time period of the solutions from contacting to administering is 30, 20, 10, or 5 seconds or less.

2. The method of claim 1 wherein the intravenous infusion solution is 0.9% sodium chloride in Water for Injection (WFI); 0.9% sodium chloride and 5% dextrose in Water for Injection (WFI); or 0.45% sodium chloride and 2.5% dextrose in Water for Injection (WFI).

3. The method of claim 1 wherein the intravenous infusion solution has a flow rate about 0.8 to about 50.0 ml/min.

4. The method of claim 1 wherein the second solution comprising the nitrogen mustard compound has a flow rate from about 0.08 to about 8.0 ml/min.

5. The method of claim 1 wherein the mixing is by gravity, agitation, shear force, or convection.

6. The method of claim 1, wherein the nitrogen mustard compound is at a concentration of about 0.2, 0.3, 0.4, 0.6, 0.8, 1.0, 1.2, 1.5, 2.0, 2.5, 3.0 or 4.0 mg/mL in the mixed solution.

7. The method of claim 1 wherein the nitrogen mustard compound is selected from the group consisting of cyclophosphamide, chlorambucil, carmustin, melphalan, uramustine, ifosfamide, mechlorethamine, lomustine and salts and combinations thereof.

8. The method of claim 1 wherein the nitrogen mustard compound is bendamustine.

9. The method of claim 1 wherein the nitrogen mustard compound is bendamustine hydrochloride.

10. The method of claim 1 wherein the second solution further comprises a saccharide excipient or a saccharide alcohol excipient.

11. The method of claim 1 wherein the second solution further comprises an excipient selected from the group consisting of mannitol, maltitol, sorbitol, erythritol, xylitol, lactitol, lactose, sucrose, glycose, maltose, trehalose, dextrose, and combinations thereof.

12. The method of claim 1 wherein the second solution comprises mannitol.

13. The method of claim 10 wherein the weight ratio of nitrogen mustard compound to excipient in the mixed solution is between 5:1 to about 1:20.

14. The method of claim 10 wherein the weight ratio of nitrogen mustard compound to excipient in the mixed solution is about 1:1.8.

15. The method of claim 10 wherein the weight ratio of nitrogen mustard compound to excipient in the mixed solution is about 1:1.7.

16. The method of claim 10 wherein the weight ratio of nitrogen mustard compound to excipient in the mixed solution is about 1:1.2.

17. The method of claim 1 wherein the second solution comprises a polymer excipient.

18. The method of claim 1 wherein the second solution further comprises a polymer excipient selected from the group consisting of vinylpyrrolidone, hydroxypropyl methyl cellulose, hydroxypropyl methyl cellulose acetate succinate (HPMC-AS), ethylene glycol, propylene glycol, propylene carbonate, vinyl acetate, vinyl propionate, vinyl caprolactame, cellulose acetate, ethyl cellulose, methyl methacrylate, methacrylic acid, polymers and co-polymers thereof.

19. The method of claim 1, wherein the second solution further comprises a solvent selected from the group consisting of Water for Injection (WFI), n-propanol, ethanol, isopropanol, n-butanol, ethyl acetate, dimethyl carbonate, acetonitrile, dichloromethane, methyl ethyl ketone, methyl isobutyl ketone, 1-pentanol, methyl acetate, carbon tetrachloride, dimethyl acetamide, hexafluoroacetone, chlorobutanol, dimethyl sulfone, acetic acid, cyclohexane, n-methyl-2-pyrrolidone (NMP), dimethylsulfoxide (DMSO), dimethylformamide (DMF), and mixtures thereof.

20. The method of claim 1 wherein the second solution comprises bendamustine hydrochloride at a concentration of about 30, 15, 10, 5, 2.5, or 1 mg/ml, and less than 3.5 or 3.0 or 2.5% total bendamustine degradation products, other than hydrolysis degradants, relative to bendamustine.

21. The method of claim 1 wherein the mixed solution comprises about 0.9% sodium chloride, about 0.8, 0.6, 0.4, or 0.2 mg/ml bendamustine hydrochloride, and less than 3.5 or 3.0 or 2.5% total bendamustine degradation products, relative to bendamustine, and is substantially free of hydrolysis degradants.

22. The method of claim 1 wherein the mixed solution comprises about 0.9% sodium chloride, about 0.8, 0.6, 0.4, or 0.2 mg/ml bendamustine hydrochloride, and less than 3.5 or 3.0 or 2.5% total bendamustine degradation products, relative to bendamustine, and is substantially free of HP1.

23. The method of claim 1, wherein the mixing the solutions is in a continuous mode of operation.

24. The method of claim 1, wherein the administering is over a time period of 5, 10, 15, 20, 30, 45, or 60 minutes.

25. The method of claim 1, wherein the flow rate for the intravenous infusion solution is from about 0.8 to about 50.0 ml/min, and the flow rate for the second solution is from about 0.08 to about 8.0 ml/min.

26. The method of claim 25, wherein the flow rates provide a controlled concentration of the nitrogen mustard compound in the mixed solution.

* * * * *